(12) United States Patent
Ahmed

(10) Patent No.: US 8,632,489 B1
(45) Date of Patent: Jan. 21, 2014

(54) IMPLANTABLE MEDICAL ASSEMBLY AND METHODS

(76) Inventor: A. Mateen Ahmed, Claremont, CA (US)

(*) Notice: Subject to any disclaimer, the term of this patent is extended or adjusted under 35 U.S.C. 154(b) by 0 days.

(21) Appl. No.: 13/334,363

(22) Filed: Dec. 22, 2011

(51) Int. Cl.
A61M 5/00 (2006.01)

(52) U.S. Cl.
USPC .................................. 604/9; 604/8

(58) Field of Classification Search
USPC ................. 604/8–10, 521, 289, 290
See application file for complete search history.

(56) References Cited

U.S. PATENT DOCUMENTS

| | | | |
|---|---|---|---|
| 4,362,681 A | 12/1982 | Spector et al. | |
| 4,761,232 A | 8/1988 | Bright | |
| 5,017,408 A | 5/1991 | Kozak | |
| 5,024,671 A | 6/1991 | Tu et al. | |
| 5,073,344 A | 12/1991 | Smith et al. | |
| 5,181,903 A | 1/1993 | Vann et al. | |
| 5,314,471 A | 5/1994 | Brauker et al. | |
| 5,370,607 A | 12/1994 | Memmen | |
| 5,432,100 A | 7/1995 | Smith et al. | |
| 5,433,748 A | 7/1995 | Wellisz | |
| 5,466,258 A | 11/1995 | Rubin | |
| 5,466,259 A | 11/1995 | Durette | |
| 5,489,306 A | 2/1996 | Gorski | |
| 5,545,226 A | 8/1996 | Wingo et al. | |
| RE35,390 E | 12/1996 | Smith | |
| 5,601,094 A | 2/1997 | Reiss | |
| 5,616,118 A | 4/1997 | Ahmed | |
| 5,665,114 A | 9/1997 | Weadlock et al. | |
| 5,713,888 A | 2/1998 | Neuenfeldt et al. | |
| 5,713,955 A | 2/1998 | Durette | |
| 5,716,660 A | 2/1998 | Weadlock et al. | |
| 5,722,948 A | 3/1998 | Gross | |
| 5,743,274 A | 4/1998 | Peyman | |
| 5,762,840 A | 6/1998 | Tsai | |
| 5,800,512 A | 9/1998 | Lentz et al. | |
| 5,807,302 A | 9/1998 | Wandel | |
| 5,824,046 A | 10/1998 | Smith et al. | |
| 5,824,073 A | 10/1998 | Peyman | |
| 5,873,196 A | 2/1999 | Hoffmann et al. | |
| 5,876,435 A | 3/1999 | Swords et al. | |
| 5,882,354 A | 3/1999 | Brauker et al. | |
| 5,908,447 A | 6/1999 | Schroeppel et al. | |
| 5,922,024 A | 7/1999 | Janzen et al. | |
| 5,941,909 A | 8/1999 | Purkait | |
| 5,964,804 A | 10/1999 | Brauker et al. | |

(Continued)

OTHER PUBLICATIONS

Hyun Bong Bae, MD et al, A membranous Drainage Implant in Glaucoma Filtering Surgery: Animal Trial, Kor. J. Ophthalmol. vol. 2:49-56, 1988.

(Continued)

Primary Examiner — Philip R Wiest
(74) Attorney, Agent, or Firm — John J. Connors; Connors & Assoc pc

(57) ABSTRACT

An implantable medical assembly includes a cover having a porous chamber. Enclosed within the chamber is a medical device through which aqueous body fluid flows from an outlet of the device into the chamber. The chamber is formed at least in part from a porous material that promotes vascularization and inhibits fibrotic encapsulation upon implantation and that allows aqueous body fluid in the chamber to flow through the porous material into body tissue in which the assembly is implanted. The chamber has a pair of walls that are spaced apart at a first portion of the chamber at or near the outlet and converge at a second portion of the chamber downstream of the outlet.

6 Claims, 14 Drawing Sheets

(56) References Cited

U.S. PATENT DOCUMENTS

| | | | |
|---|---|---|---|
| 5,972,366 | A | 10/1999 | Haynes et al. |
| 5,977,204 | A | 11/1999 | Boyan et al. |
| 5,977,431 | A | 11/1999 | Knapp et al. |
| 6,018,095 | A | 1/2000 | Lerch et al. |
| 6,030,558 | A | 2/2000 | Smith et al. |
| 6,058,590 | A | 5/2000 | Roberts et al. |
| 6,060,640 | A | 5/2000 | Pauley et al. |
| 6,063,117 | A | 5/2000 | Perry |
| 6,068,478 | A | 5/2000 | Grande et al. |
| 6,069,295 | A | 5/2000 | Leitao |
| 6,083,264 | A | 7/2000 | Wood et al. |
| 6,099,565 | A | 8/2000 | Sakura, Jr. |
| 6,110,205 | A | 8/2000 | Nies |
| 6,146,686 | A | 11/2000 | Leitao |
| 6,181,973 | B1 | 1/2001 | Ceron et al. |
| 6,182,668 | B1 | 2/2001 | Tweden et al. |
| 6,187,043 | B1 | 2/2001 | Ledergerber |
| 6,203,573 | B1 | 3/2001 | Walter et al. |
| 6,228,111 | B1 | 5/2001 | Tormala et al. |
| 6,235,225 | B1 | 5/2001 | Okada et al. |
| 6,277,150 | B1 | 8/2001 | Crauley |
| 6,281,015 | B1 | 8/2001 | Mooney et al. |
| 6,290,982 | B1 | 9/2001 | Seppala et al. |
| 6,306,169 | B1 | 10/2001 | Lee et al. |
| 6,315,796 | B1 | 11/2001 | Eaton |
| 6,332,775 | B1 | 12/2001 | Gordils Wallis |
| 6,344,496 | B1 | 2/2002 | Niederauer et al. |
| 6,352,708 | B1 | 3/2002 | Duran et al. |
| 6,399,188 | B1 | 6/2002 | Smith et al. |
| 6,409,697 | B2 | 6/2002 | Eno |
| 6,520,997 | B1 | 2/2003 | Pekkarinen |
| 6,521,284 | B1 | 2/2003 | Parsons |
| 6,534,197 | B2 | 3/2003 | Noda et al. |
| 6,540,780 | B1 | 4/2003 | Zilla et al. |
| 6,551,608 | B2 | 4/2003 | Yao |
| 6,553,681 | B2 | 4/2003 | Ekholm, Jr. et al. |
| 6,554,857 | B1 | 4/2003 | Zilla et al. |
| 6,571,130 | B1 | 5/2003 | Ljungstrom et al. |
| 6,591,838 | B2 | 7/2003 | Durgin |
| 6,592,513 | B1 | 7/2003 | Kroll et al. |
| 6,626,823 | B1 | 9/2003 | Campbell et al. |
| 6,629,997 | B2 | 10/2003 | Mansmann |
| 6,632,503 | B1 | 10/2003 | Shikinami et al. |
| 6,673,075 | B2 | 1/2004 | Santilli |
| 6,673,108 | B2 | 1/2004 | Zilla |
| 6,699,210 | B2 | 3/2004 | Williams et al. |
| 6,702,857 | B2 | 3/2004 | Brauker |
| 6,709,452 | B1 | 3/2004 | Valimaa |
| 6,710,093 | B2 | 3/2004 | Yao et al. |
| 6,783,499 | B2 | 8/2004 | Schwartz |
| 6,815,384 | B2 | 11/2004 | Ishikawa |
| 6,833,153 | B1 | 12/2004 | Roorda |
| 6,840,960 | B2 | 1/2005 | Bubb |
| 6,849,214 | B2 | 2/2005 | Patil |
| 6,875,166 | B2 | 4/2005 | Kroll |
| 6,881,198 | B2 * | 4/2005 | Brown .............. 604/8 |
| 6,916,304 | B2 | 7/2005 | Eno |
| 6,995,013 | B2 | 2/2006 | Connelly |
| RE39,069 | E | 4/2006 | Faour |
| 7,033,388 | B2 | 4/2006 | Zilla |
| 7,047,981 | B2 | 5/2006 | Durgin |
| 7,066,962 | B2 | 6/2006 | Swords |
| 7,077,821 | B2 | 7/2006 | Durgin |
| 7,094,226 | B2 | 8/2006 | Yaacobi |
| 7,097,451 | B2 | 8/2006 | Tang |
| 7,118,695 | B2 | 10/2006 | Lin |
| 7,131,997 | B2 | 11/2006 | Bourne |
| 7,147,846 | B2 | 12/2006 | Anderson |
| 7,192,450 | B2 | 3/2007 | Brauker |
| 7,201,917 | B2 | 4/2007 | Malaviya |
| 7,226,615 | B2 | 6/2007 | Yuksel |
| 7,244,270 | B2 | 7/2007 | Lesh |
| 7,314,636 | B2 | 1/2008 | Caseres |
| 7,338,517 | B2 | 3/2008 | Yost |
| 7,378,144 | B2 | 5/2008 | DeMeo |
| 7,390,498 | B2 | 6/2008 | Dalal |
| 7,399,312 | B2 | 7/2008 | Bicek |
| 7,431,734 | B2 | 10/2008 | Danoff |
| 7,500,988 | B1 | 3/2009 | Butaric |
| 7,507,469 | B2 | 3/2009 | Mao et al. |
| 7,524,335 | B2 | 4/2009 | Slivka |
| 7,534,448 | B2 | 5/2009 | Saltzman |
| 7,550,091 | B2 | 6/2009 | Beaty |
| 7,588,686 | B2 | 9/2009 | Jensen |
| 7,632,228 | B2 | 12/2009 | Brauker |
| 7,632,306 | B2 | 12/2009 | Zilla |
| 7,648,726 | B2 | 1/2010 | Liu |
| 7,655,047 | B2 | 2/2010 | Swords |
| 7,674,517 | B2 | 3/2010 | Ramsey et al. |
| 7,682,540 | B2 | 3/2010 | Boyan |
| 7,699,882 | B2 | 4/2010 | Stamper |
| 7,727,274 | B2 | 6/2010 | Zilla |
| 7,731,988 | B2 | 6/2010 | Thomas |
| 7,789,908 | B2 | 9/2010 | Sowinski |
| 7,795,346 | B2 | 9/2010 | Martin |
| 7,803,178 | B2 | 9/2010 | Whirley |
| 7,803,183 | B2 | 9/2010 | Kutryk |
| 7,806,922 | B2 | 10/2010 | Henderson |
| 7,807,210 | B1 | 10/2010 | Roorda |
| 7,811,268 | B2 | 10/2010 | Maldon Ado Bas |
| 7,815,826 | B2 | 10/2010 | Serdy |
| 7,815,923 | B2 | 10/2010 | Johnson |
| 7,833,615 | B2 | 11/2010 | Ramsey |
| 7,850,862 | B2 | 12/2010 | Amrich |
| 7,854,958 | B2 | 12/2010 | Kramer |
| 7,901,462 | B2 | 3/2011 | Yang |
| 7,910,124 | B2 | 3/2011 | Boyan |
| 7,939,000 | B2 | 5/2011 | Edwin |
| 7,943,162 | B2 | 5/2011 | Missel |
| 7,998,202 | B2 | 8/2011 | Lesh |
| 7,998,523 | B2 | 8/2011 | Lerf |
| 8,002,830 | B2 | 8/2011 | Boyan |
| 8,007,823 | B2 | 8/2011 | Favis |
| 8,025,896 | B2 | 9/2011 | Malaviya |
| 8,062,739 | B2 | 11/2011 | Liu |
| 8,066,770 | B2 | 11/2011 | Rivard |
| 8,066,778 | B2 | 11/2011 | Meridew |
| 8,071,124 | B2 | 12/2011 | Yuksel |
| 8,118,867 | B2 | 2/2012 | Perry |
| 8,118,877 | B2 | 2/2012 | Brauker |
| 8,124,187 | B2 | 2/2012 | Su |
| 8,128,689 | B2 | 3/2012 | Weber |
| 8,128,706 | B2 | 3/2012 | Kaigler |

OTHER PUBLICATIONS

McElwain et al, A Model of Vascular Compression in Solid Tumours, J. theor. Biol. (1979) 78, 405-415.

James K. Arthur et al, A PIV Study of Fluid Flow Through Parallel Communicating Layers of Porous Media, SCA2008-32.

Paul Sabini, MD et al, Arch Facial Plast Surg, Jan.-Mar. 2000, vol. 2, No. 1, pp. 27-33.

Hagery et al, Cellular Proliferation & Macrophage Populations Associated With Implanted Expanded Polytetrafluoroethylene & Polyethyleneterphthalate , 2000 John Wiley & Sons.

Robert S. Kellar et al, Characterization of Angiogenesis and Inflammation Surrounding ePTFE Implanted on the Epicardium, 2002, Wiley Periodicals, Inc.

Kim et al, Clinical Experience of e-PTFE Membrane Implant Sugery for Refractory Glaucoma, Jan. 2003, vol. 87(1), pp. 63-70.

Berglund/Galis, Designer Blood Vessels and Therapeutic Revascularization, Journal List Br J Phamacol, vol. 140(4) Oct. 2003.

Wenguo Cui et al, Electrospun Nanofibrous Materials for Tissue Engineering and Drug Delivery, Science & Technology of Advanced Materials, 2010.

Carl A. Boswell et al, Evaluation of an Aqueous Drainage Glaucoma Device Constructed of ePTFE, 1999 John Wiley & Sons, Inc.

DeCroos et al, Expanded Polytetrafluoroethylene Membrane Alters Tissue Response to Implanted Ahmed Glaucoma Valve, Current Eye Research, 34, 562-567, 2009.

Kuzman/Soboleva, Flow Through a Porous Medium With Multiscale Log-Stable Permeability, Proceedings of Institute of NAS of Ukraine, 2004, vol. 50, Part 3, 1396-1403.

(56) References Cited

OTHER PUBLICATIONS

Brewster et al, Growing a Living Blood Vessel:Insights for the Second Hundered Years, Biomaterials, Dec. 2007; 28(34) 5028-5032.
Andrade Jr. et al, Inertial Effects on Fluid Flow Through Disordered Porous Media, vol. 82, No. 26, Jun. 28, 1999.
Seed, How We Build It and Why It Behaves the Way It Does, Jul. 13, 2010.
Hing et al, Mediation of Bone Ingrowth in Porous Hydroxyapatite-Bone Graft Substitutes, 2003 Wiley Periodicals, Inc.
Kathryn Adele Maiellaro, Microfabricated Silicon Microchannels for Cell Rheology Study, Univ. of Florida, 2003.
Sandor/Adams, Minimum Blood Vessel Diameter Measured by Magification Angiography, 1979 American Roentgen Ray Society.
Sabini et al, Modulation of Tissue Ingrowth Into Porous High-Density Polyethylene Implants With Basic Fiborblast Growth Factor & Autolongous Blood Clot American Med Assoc 2000.
Druecke et al, Neovascularization of Poly(ether ester)Block-Copolymer Scaffolds in vivo: Long Term Investigations Using Intravital Flourescent Microscopy, Wiley Periodical 2003.
Ahmed et al, Preliminary Studies, Phase/Progress Report, Phase 1 beginiing Sep. 1, 2004, ending Feb. 28, 2005.
Masay/Ayamamoto et al, Promotion of Fibrovascular Tissue Ingrowth Into Porous Sponges by Basic Fibroblast Growth Factor, Kluwer Academic Publishers, 2000.
Qu Weilin, et al, Pressure-Driven Water Flows in Trapezoidal Silicon Microchannels, Elsevier Science Ltd, 1999.
Zhen Wang, et al, Role of the Porous Sctructure of the Bioceramic Scaffolds in Bone Tissue Engineering, Nature Precedings, Jan. 9, 2010.
Isenberg et al, Small-Diameter Artificial Arteries Engineered in Vitro, American Heart Assoc. Inc., 2006.
Guldberg et al, 3D Imaging of Tissue Integration With Porous Biomaterials, Elsevier Ltd, 2008.
Cheng et al, The Expression of Cross-Linked Elastin by Rabbit Blood Vessel Smooth Muscle Cells Cultured in Polyhydroxyalkonoate Scaffolds, Biomaterials 29, 2008 4187-4194.
Theracyte, Inc., Theracyte System, Theracyte, Inc., 2000.
Eastridge, Feldman, Quantification of Vascualr Ingrowth Into Dacron Velour, Jan. 1, 1991.
Takahashi, Adsorption of Basic Fibroblast Growth Factor Onto Dacron Vascular Prosthesis and Its Biological Efficacy, Revised Feb. 1997.
Jallet, Novel Synthetic Meshwork for Glaucoma Treatment. I Design & Prliminary in Vitro & in Vivo Evaluation of Various Expanded Poly(tetrafluoroethylene) Materials Apr. 14, 1999.
Cillino, E-PTFE (Gore-Tex)Implant With or Without Low-Dosage Mitomycin-C As an Adjuvant in Penetrating Glaucoma Surgery 2 yr Randomized Clinical Trial, Acta Ophthalmol. 2008.
Lee, Flow Correlated Percolation During Vascular Remodeling in Growing Tumors, Feb. 7, 2006, The American Physical Society.
Denekamp, Vascular Endothelium As the Vulnerable Element in Tumors, Jan. 30, 1984.
Scalerandi, Inhibition of Vascularization in Tumor Growth, Nov. 18, 2002, the American Physical Society.
Plank, Lattice an d Non-Lattice Models of tumor Angiogenesis, School of Mathematics, University of Leeds, Nov. 2004.
Salzmann, Inflammation and Neovascularization Associated With Clinically Used Vascular Prosthetic Materials, Cardiovascular Pathology, vol. 8, No. 2, Mar./Apr. 1999.
Jeschke, Polyurethane Vascular Prostheses Decreases Neointimal Formation Compared With Expanded Polytetrafluoroethylene, Journal of Vascular Surgery, Jan. 1999.
Muller Towards an Introperative Engineering of Osteogenic & Vasculogenic Grafts From The Stromal Vascular Fraction of Human Adipose Tissue European Cells&Material vol. 19 2010.
Vara, Cardiovascular Tissue Engineering:State of the Art Ingenierie Tissulaire Applique Aux Vaisseaux Sanguins: etat de l'art, Jan. 25, 2005.
Motomiya, Effect of Hydroxyapatite Porous Characteristics on Healing Outcomes in Rabbit Posterolateral Spinal Fusion Model, Sep. 27, 2007.
Hing, Microporosity Enhances Bioactivity of Synthetic Bone Graft Substitutes, Journal of Materials Science, Materials in Medicine 16, 2005.
Hoffmann, Vessel Size Measurements in Angiograms: Manual Measurements, Med. Phys. 30 (4) Apr. 2003.
Sclafani, Modulation of Wound Response & Soft Tissue Ingrowth in Synthetick & Allogeneic Implants With Platelet Concentrate, American Medical Assoc. 2005.
Park, Effect of Basic Filroblast Growth Factor on Fibrovascular Ingrowth Into Porous Polyethylene Anophthalmic Socket Implants, Korean J Ophthalmol, vol. 19:1-8, 2005.
Ring, Analysis of Neovascularization of PEGT/PBT-Copolymer Dermis Substitutes in Balb/C-Mice, Elsevier Ltd and ISBI, 2005.
Laschke, Incorporation of Growth Factor Containing Matrigel Promotes Vascularization of Porous PLGA Scaffolds, Wiley Periodicals, 2007.
Ring, Improved Neovascularization of PEGT/PBT Copolymer Matrices in Response to Surface Modification by Biomimetic Coating, European Surgical Research, Feb. 1, 2007.
Kimura, Time Course of de Novo Adipogenesis in Matrigel by Gelatin Microspheres Incorporating Basic Fibroblast Growth Factor, Tissue Engineering, vol. 8, No. 4, 2002.
Takemoto, Preparation of Collagen/Gelatin Sponge Scaffold for Sustained Release of bFGF, Tissue Engineering: Part A, vol. 14, No. 10, 2008.
Tschoeke, Tissue-Engineered Small-Caliber Vascular Graft Based on a Novel Biodegradable Composite Fibrin-Polyacitide Scaffold, Tissue Engineering Part A, vol. 15, No. 8, 2009.
Stekelenburg Dynamic Straining Combined With Fibrin Gel Cell Seeding Improves Strenght of Tissue-Engineered Small-Diameter Vascular Grafts Tissue Engineering Part A vol. 1 2000.
Jones, Quantifying the 3D Macrostructure of Tissue Scaffolds, Journal of Material Science, Mater Med. 2009.
Chen, Synthesis, Characterization and Cell Compatability of Novel Poly (ester urethane)s Based on Poly(3-hydroxybutyrate-co-4-hydroxybutyrate)and Poly(3-hydroxybutyrate-co-3-hydroxyhexanoate) Prepared by Melting Polymerization, Journal of Biomaterials Science 20, 2009, 1451-1471).
Wang, Guided Growth of Smooth Muscle Cell OnPoly3-hydroxybutyrate-co-3-hydroxyhexanoate) Scaffolds With Uniaxial Micotubular Structures, Wiley Periodicals, Inc., 2008.
Williams, Differential Healing and Neovascularization of ePTFE Implants in Subcutaneous Versus Adipose Tissue, Journal of Biomedical Materials Research, vol. 35,473-481, 1997.
Boswell, Denucleation Promotes Neovascularization of ePTFE in vivo, Journal of Biomaterial Science, Polymere Edn. vol. 10 No. 3, 319-329, 1999.
Trocciola, The Development of Endotension Is Associated With Increased Transmission of Pressure & Serous Components in Porous Expanded Polytetrafluoroethylene stent-grafts: Characterization Using a Canine Model, The Society for Vascular Surgery, 2006.
Andrews, Vascular Prostheses: Performance Related to Cell-Shear Responses, Journal of Surgical Research, 2008.
Williams, Covalent Modification of Porous Implants Using Extracellular Matrix Proteins to Accelerate Neovascularization, Apr. 6, 2006 Wiley Publications.
Gruionu, Encapsulation of ePTFE in Prevascularized Collagen Leads to Peri-Implant Vascularization With Reduced Inflammation, Dec. 1, 2010, Journal Bio Med.
Kidd, Angiogenesis and Neovascularization Associated With Extracelllular Matrix-Modified Porous Implants, Jun. 14, 2001, John Wiley & Sons, Inc.
Kidd, Laminin-5-Enriched Extracellular Matrix Accelerates Angiogenesis and Neovascularization in Association with ePTFE, Feb. 19, 2004, Wiley Periodicals.

(56) References Cited

OTHER PUBLICATIONS

Ucuzian, In Vitro Models of Angiogenesis, World Journal of Surgery, 2007.
Grundmann, Arteriogenesis: Basic Mechanisms and Therapeutic Stimulation, Blackwell Publishing Company, 2007.
Brey, Therapeutic Neovascularization Contributions From Bioengineering, Mary Ann Liebert, Inc. vol. 11, No. 3/4, 2005.
Salzmann et al, The Effects of Porosity on Endothelialization of ePTFE Implanted in Subcutaneous & Adipose Tissue, Journal of Biomedical Meterials Research vol. 34 463-476 1997.
Lokmic et al, Vascularization of Engineered Constructs, Abstract, Sep. 30, 2010.
DeCroos et al, In Vitro Fluid dynamics of the Ahmed Glaucoma Valve Modified With Expanded Polytetrfluoroethylene, Informa Healthcare USA, Inc. 2001.

* cited by examiner

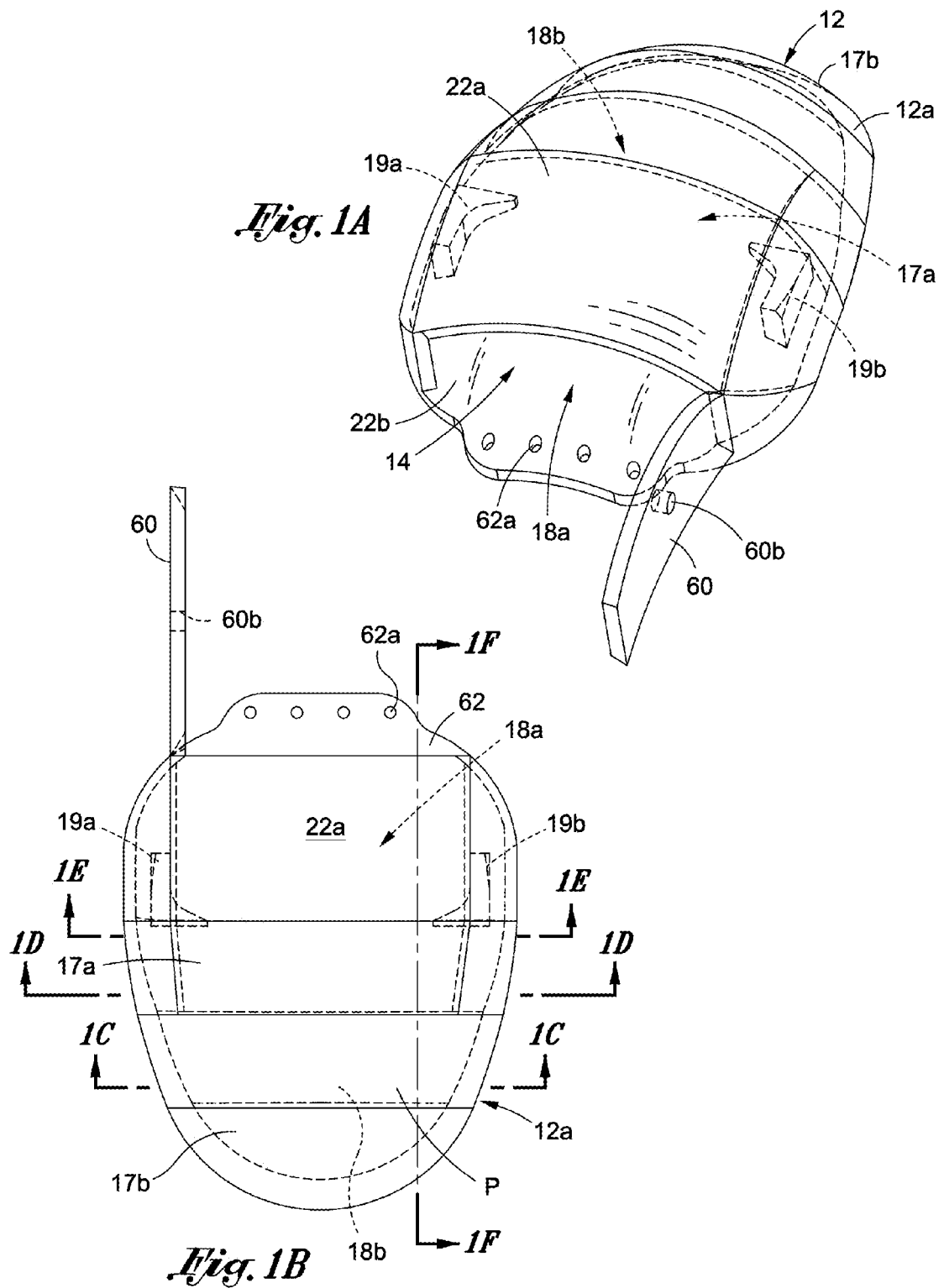

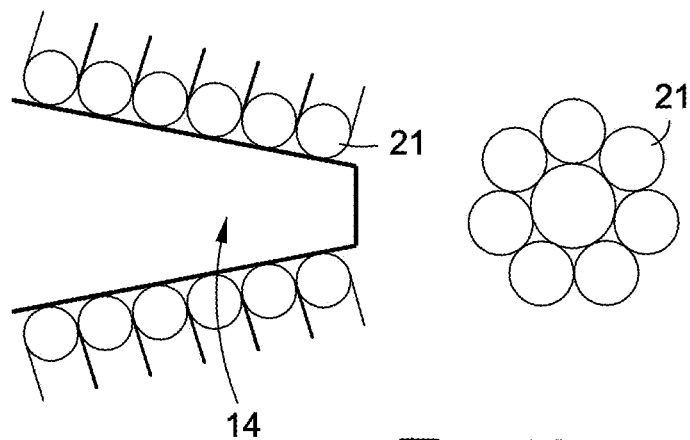
Fig. 13
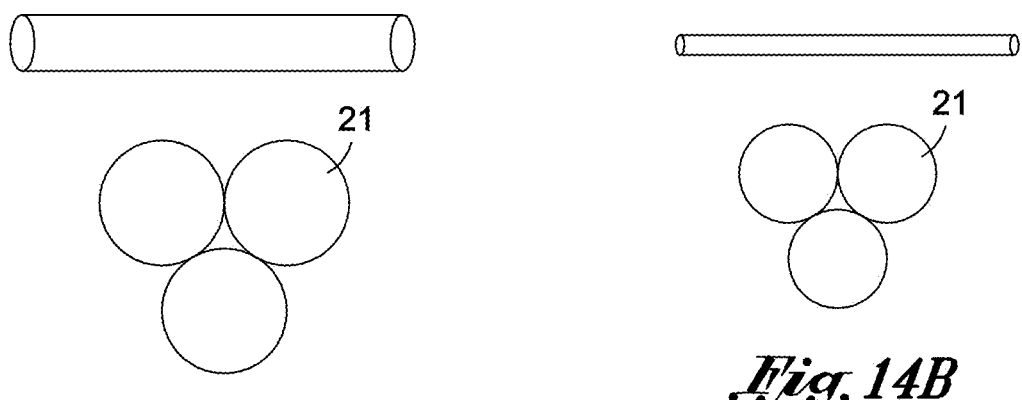
Fig. 14A
Fig. 14B
Fig. 14C

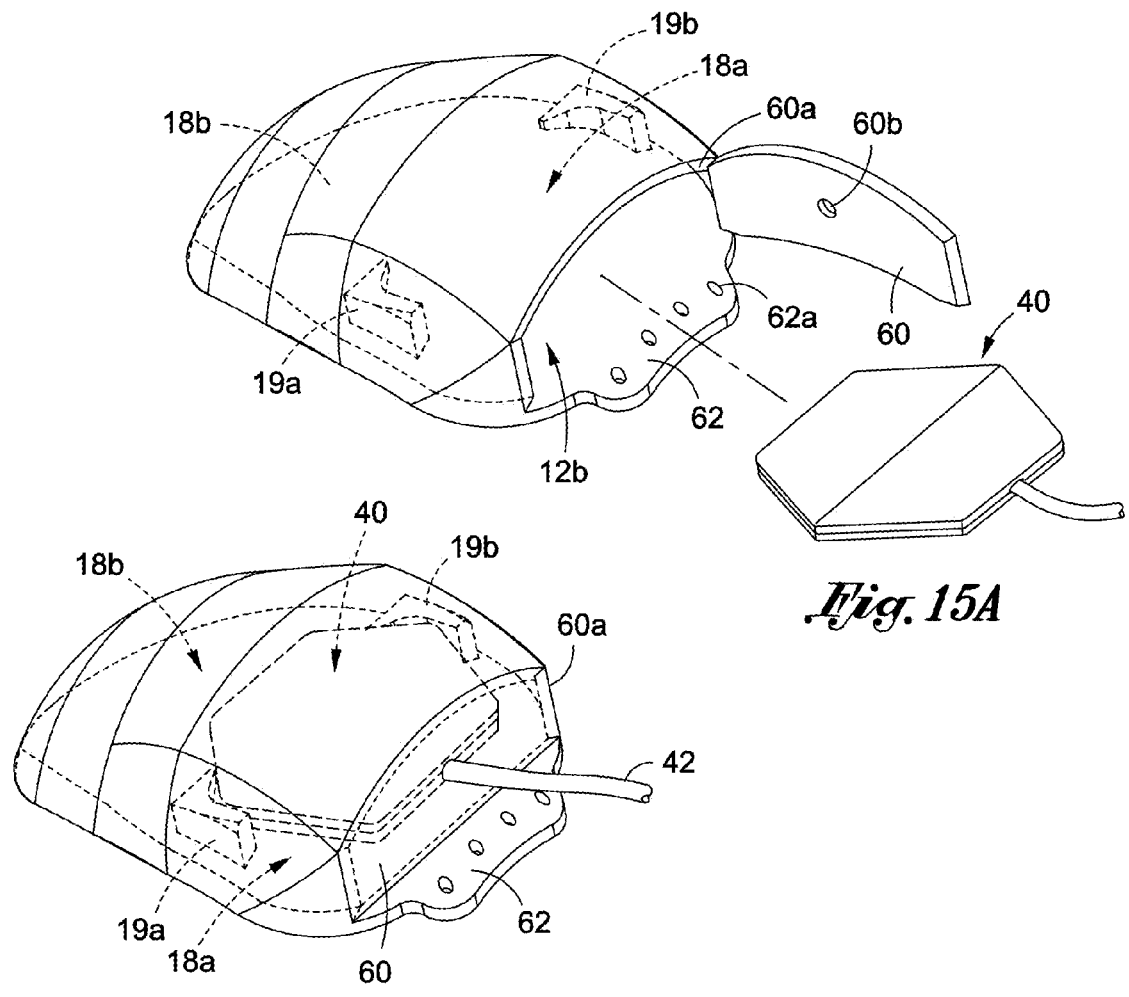
Fig. 15A
Fig. 15B
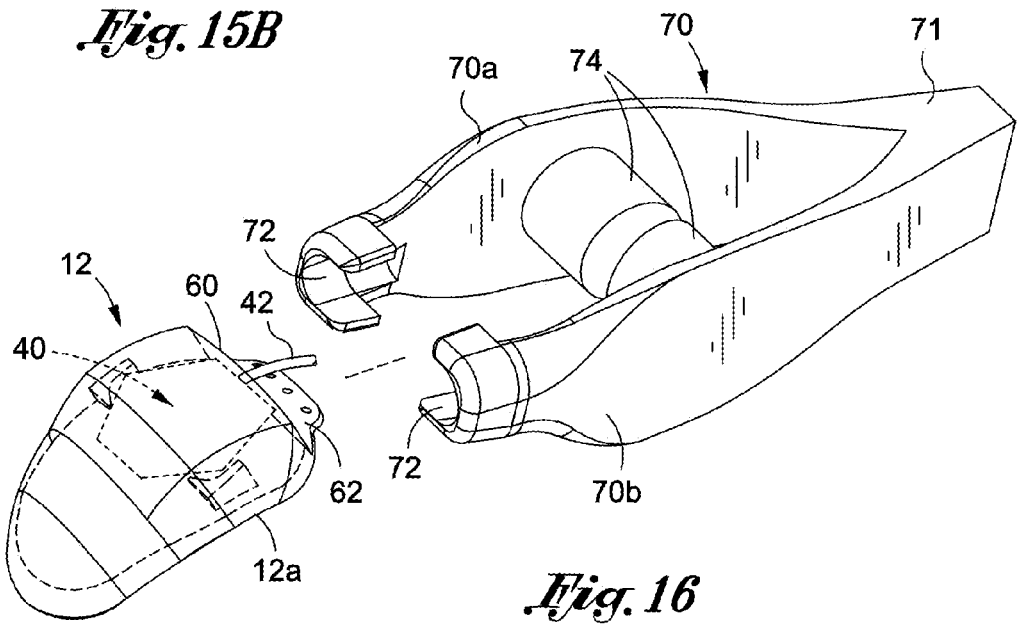
Fig. 16

IMPLANTABLE MEDICAL ASSEMBLY AND METHODS

BACKGROUND

During trabeculectomy, or even glaucoma implant surgery, when aqueous humor is drained from the anterior chamber of the eye to the outside tissue, it causes a severe tissue reaction. One tissue reaction is to encapsulate the aqueous humor by means of fibrous tissue growth commonly known as bleb formation. Avoiding forming a bleb, or minimizing the rate of growth of a bleb around an implanted medical device, especially a glaucoma valve, is highly desirable. After the bleb is formed over an implanted glaucoma device, encapsulating it, the intraocular pressure (IOP) in the eye increases because the fluid in the bleb gets locked in. If the bleb is thin enough and there is sufficient blood vessel growth surrounding the fibrous tissue, the aqueous humor is then carried through the blood vessels back into circulation. Even though this phenomenon is helpful for aqueous transport from the bleb into the subcutaneous tissue, there is still resistance to aqueous flow from the eye into circulation. The density, wall thickness, and type of collagen formation of a bleb encasing an implanted glaucoma valve ultimately become the controlling factors of the intraocular pressure in the anterior chamber of the eye. The greater the outside resistance imposed by the bleb, the greater the intraocular pressure (IOP) as implanted medical devices utilize differential pressure.

The second most common cause of blindness in the world is glaucoma, affecting about 53 million around the world. In glaucoma the blood supply to the retina is reduced or almost stopped due to high intraocular pressure in the eye. This results in retinal ganglion death and optic nerve atrophy. The normal pressure in the human eye is between 10 to 21 millimeters of mercury (mm Hg). Once the onset of glaucoma occurs, control of intraocular pressure (IOP) is very important to prevent further vision loss. It is desired to keep the IOP between 10 to 15 mm Hg. Some implant devices are deficient because they have a high rate of hypotony. An IOP below 5 mm of Hg indicates hypotony is occurring. The Molteno glaucoma implant device sold by IOP Ophthalmics of Costa Mesa, Calif., the Barlvealdt glaucoma implant device sold by Abbot Medical Optics of Santa Ana, Calif., and the Express shunt sold by Alcon of Forth Worth, Tex., have a relatively high rate of hypotony. The Ahmed glaucoma valve sold by New World Medical, Inc. of Rancho Cucamonga, Calif., is a self-regulating implantable valve that has successfully reduced the incidence of hypotony. The Ahmed glaucoma valve is discussed in U.S. Pat. No. 5,071,408, illustrating how it is implanted in the sclera and controls the IOP to within the desired range of 10 to 15 mm Hg. In the Ahmed glaucoma valve fluid from the anterior chamber of the eye flows through a valve outlet onto a plate, and then through the bleb tissue and into blood vessels that carry the fluid to the rest of the patient's body. In many patients the drainage of aqueous body fluid onto subcutaneous tissue leads to the formation of a thick, non-percolating bleb enclosing the valve and eventually preventing its operation.

Bleb formation with excessive fibrosis may inhibit or prevent the intended operation of such medical devices. In the case of non-valve glaucoma devices, all need a bleb to maintain proper intraocular pressure (IOP). Usually the pressure in the bleb is less than the IOP in the anterior chamber of the eye. The walls of the bleb allow the aqueous to permeate into the blood stream through blood vessels that grow into the bleb. Most of these devices fail because the bleb walls become too thick and stop the percolation of aqueous out of the system. Consequently, the external resistance becomes too high for the aqueous to drain out of the anterior chamber.

Avoiding or minimizing bleb formation is also important when implanting other medical devices beside ophthalmological devices. For example, implantable self-regulating valves may be used in neurology where cerebrospinal fluid is drained through a shunt device that drains into the peritoneum.

SUMMARY

My implantable medical assembly includes a medical device within a cover having a tapered, porous, cavity-like internal chamber. The cover acts as an enclosure for the medical device. My method comprises implanting my medical assembly within the body of a patient. The combination of the medical device and cover, upon implantation, allows aqueous body fluid to flow through the medical device into the cover's chamber and then flow through porous walls of the chamber into the patient's body tissue in which the assembly is implanted. The porous cover may be made by a variety of methods, for example, molded by sintering together plastic beads, by creating a scaffold and forcing the polymer through the scaffold and later dissolving the scaffold to leave a porous structure, 3D printing, joining together porous sheets, for example, by positioning on a support structure a pair of opposed sheets of a porous membrane. The beads used may be substantially spherical.

My cover has a length substantially from 8 to 25 millimeters, a width substantially from 8.75 to 16.75 millimeters, and a height substantially from 0.5 to 2.5 millimeters. The porous chamber has a length substantially from 10 to 23 millimeters. The external surface configuration of the cover is a streamline predetermined curvature that facilitates insertion into a surgical incision made for implantation, having smooth rounded edges and a tapered rounded distal end and a curvature that substantially conforms to the shape of an eyeball's exterior.

The cover's chamber has at least one porous wall and typically employs a pair of opposed porous walls each having a thickness substantially from 0.0146 to 0.148 millimeters (mm). The porous portion of the chamber has a volume substantially from 0.02 to 0.5 cubic centimeters with downstream stages having smaller volumes than upstream stages. For example in one embodiment, a first stage of the porous portion of the chamber has a volume of approximately 0.12 cubic centimeters, a second stage of the portion of the chamber has a volume of approximately 0.06 cubic centimeters, and a third stage of the porous portion of the chamber has a volume of approximately 0.02 cubic centimeters. The porous walls are curved and are spaced apart at an upstream end and merge at a downstream end. The walls may have a radius of curvature substantially from 21.5 to 38.5 millimeters, and one wall overlies the other wall, with the underlying wall having a radius of curvature greater than the overlying wall. The distance between the opposed walls decreases from the upstream end to the downstream end, with the maximum distance of separation at the upstream end being no greater than approximately 2.5 millimeters.

The cover's chamber has variable cross-sectional areas so the velocity of the aqueous body fluid flowing through the tapered chamber increases as this fluid flows from end-to-end in the chamber and through pores of the material forming at least in part the chamber. In one embodiment, the chamber has a substantially trapezoidal cross-sectional configuration taken substantially along a longitudinal reference line and its porous portion has a porosity that varies in stages with upstream stages of the chamber have a greater porosity than downstream stages of the chamber. In general, the porous portion of the chamber has pores with a diameter substantially from 1 to 400 microns. In one embodiment, the pores vary along different incremental chamber portions to encourage the growth of blood vessels having different sized diameters. Larger pores are near the upstream portion of the chamber and smaller pores are at the downstream portion of the chamber. For example, pores in a stage nearest the upstream end range in pore size substantially from 75 to 400 microns; pores in a middle stage range in pore size substantially from 50 to 200 microns; and pores in a stage nearest to the downstream end range in pore size substantially from 25 to 125 microns. Different stages of the chamber includes pores having a substantially uniform diameter with the pores in the downstream stages having diameters at least 25 percent less than a preceding stage. The ratio of the diameter of the pores and the average distance between the opposed walls in any stage remains essentially constant from the upstream end to the downstream end.

By using a porous cover, wound healing is modulated such that fibrous growth is interrupted, allowing for the growth of blood vessels that provide the aqueous fluid an easier path to get into the blood stream. This type of growth decreases the external resistance to fluid flow around the implant, helping to keep the intraocular pressure low. Such controlled flow of fluid through my implantable medical assembly assists in dissipating the fluid into the patient's macro blood circulation system via the blood stream through micro and then macro-circulation.

The medical device is seated within a device retention section of the chamber. The medical device is essentially entirely covered by the cover, expect for ancillary communication components of the medical device such as, for example, connecting tubes placing the medical device in communication with a body part of the patient to be drained of fluid. Downstream of the device retention section of the chamber is a fluid retention section of the chamber. This fluid retention section of the chamber is tapered so that the velocity of the fluid entering the chamber at or near an outlet of the enclosed medical device increases as the fluid movement progresses towards a terminal (distal) end of the chamber downstream of the outlet of the medical device.

In one embodiment the cover is formed by a pair of opposed, spaced apart walls, which may be curved to substantially conform to the curvature of the external surface of an eyeball. These walls comprise the roof and floor of my cover. At an entry end of the fluid retention section of the chamber, the walls are spaced apart a maximum distance to provide a gap, and at or near the terminal end, the walls are spaced apart a minimal distance. The maximum distance between the walls is substantially from 0.01 to 5 millimeters (mm), and the walls have predetermined thicknesses that are essentially equal, ranging substantially from 0.01 to 5 mm. The ratio of the thickness of the walls to the gap at the maximum distance between the walls ranges substantially from 1:30 to 2:1. The walls may gradually converge at or near the terminal end. The terminal end may be closed so that all the fluid entering the fluid retention section of the chamber is directed to flow through one or both opposed porous walls of the chamber. Or, the terminal end may be open so that at least some fluid flows out this terminal end. The device retention section is configured to enable the medical device to be inserted therein and held firmly in position so that aqueous body fluid flows through the device and directly into the fluid retention section of the chamber. Essentially all the fluid exiting the medical device flows through the fluid retention section.

There are several embodiments of my implantable medical assembly depending on the type of medical device being seated within the chamber. For example, as discussed above, the medical device may be a valve. Valves may be used in cardiology devices, peritoneum shunt devices, orthopedic implants, urological implants, dental implants, neurological implants, and ophthalmological implants.

One embodiment is an ophthalmological device for treating glaucoma. In this embodiment the medical device is the Ahmed glaucoma valve. This glaucoma valve comprises a non-obstructive, self-regulating pressure control system having an inlet tube coming from the anterior chamber of the eye into the anterior side of this valve system. The posterior end of the inlet tube enters a pre-tensioned valve membrane sandwiched between the top and bottom plates of this valve, forming a trapezoidal venturi cavity, having a larger inlet opening and narrowing down to smaller opening, helping to increase the velocity of fluid within this cavity, which helps to evacuate the eye fluid, thereby reducing resistance within the valve system.

This glaucoma valve is encased within the cover, which encloses essentially the entire glaucoma valve. In one embodiment the cover has a porous portion with a unique variable pore size formed from spherical beads or by another method. A portion of the cover's chamber is enlarged at an entrance or proximal end where the valve body is placed. The variable porous portion of the chamber tapers down from the proximal end towards a distal end. Thus the chamber forms an envelope with constant tapering sections between top and bottom porous walls. The chamber has sidewalls that are rigid so they support the top and bottom walls, preventing collapse of the chamber. These sidewalls may or may not be porous. The tapering of the envelope or chamber is thus configured into cross-sectional area sections that decrease gradually in area from the proximal end to the distal end.

At the proximal end the aqueous exits the glaucoma valve and enters the porous portion of the cover's chamber. The quantity of aqueous is the greatest in volume as it enters the chamber, so the porosity of the top and bottom walls here is the greatest to maximize the growth of large diameter blood vessels. A gradient of diminishing size pores is created by dividing the chamber into a plurality of regions of decreasing porosity. In one embodiment three regions are employed where the diameter of the pores is the greatest, for example, 100 microns, near the proximal end. The next area section tapers inward, so a lesser volume of aqueous flows into it, and here the diameter of the pores is intermediate in diameter between the distal and proximal ends, for example, 75 microns. In a terminal area section of the chamber, the volume of aqueous to be dissipated is the least, and here the top and bottom walls have pores of the smallest diameter, for example, 50 microns. This variable pore size of the top and bottom walls, decreasing from proximal to distal ends, helps to keep the intraocular pressure from rising above 10 to 15 millimeters (mm) of mercury (Hg). Prolonged testing of porous enclosed implants in animals and human beings demonstrated a substantial reduction in outflow resistance, indicating that the tissue surrounding the implant was more permeable to fluid compared to the controls.

The edges of the exterior of the cover are smooth, allowing the entire assembly to slide easily into a surgical incision between the sclera and tenons. There are two external suture holes provided at or near the entrance of the glaucoma valve to be sutured on the sclera, about 8-10 mm away from the limbus. Such an assembly using a cover having a chamber comprising a tapered, variable pore size wall structure will be capable of (1) reducing bleb formation by fostering the formation of variable sized blood vessels best suited to evacuate the variable area sections of the chamber and (2) allowing the intraocular pressure in the eye to remain substantially between 10 to 12 mm of Hg.

My medical assembly, cover, and implantation methods have one or more of the features depicted in the embodiments discussed in the section entitled "DETAILED DESCRIPTION OF SOME ILLUSTRATIVE EMBODIMENTS." The claims that follow define my medical assembly, cover, and implantation methods, distinguishing them from the prior art.

DESCRIPTION OF THE DRAWING

Some embodiments of my method, assembly and system are discussed in detail in connection with the accompanying drawing, which is for illustrative purposes only. This drawing includes the following figures (FIGS.), with like numerals indicating like parts:

FIG. 1A is a perspective view of a cover for one embodiment of my implantable medical assembly.

FIG. 1B is a top plan view of the cover shown in FIG. 1A.

FIG. 13 is a schematic diagram of porous material comprising plastic beads fused together.

FIGS. 14A through 14C depict blood vessels of varying diameters that would be growing into pores of greater and smaller diameters.

FIG. 15A is a perspective view of the cover shown in FIG. 1A having a proximal door in an open position and positioned to receive the glaucoma valve shown in FIG. 2.

FIG. 15B is a perspective view similar to that of FIG. 15A showing the glaucoma valve within the cover and the proximal door in a closed position.

FIG. 16 is a perspective view of forceps that may be used in implanting my medical assembly depicted in FIG. 15B and aligned to be grasped by the forceps.

DETAILED DESCRIPTION OF SOME ILLUSTRATIVE EMBODIMENTS

General

Figure 1:
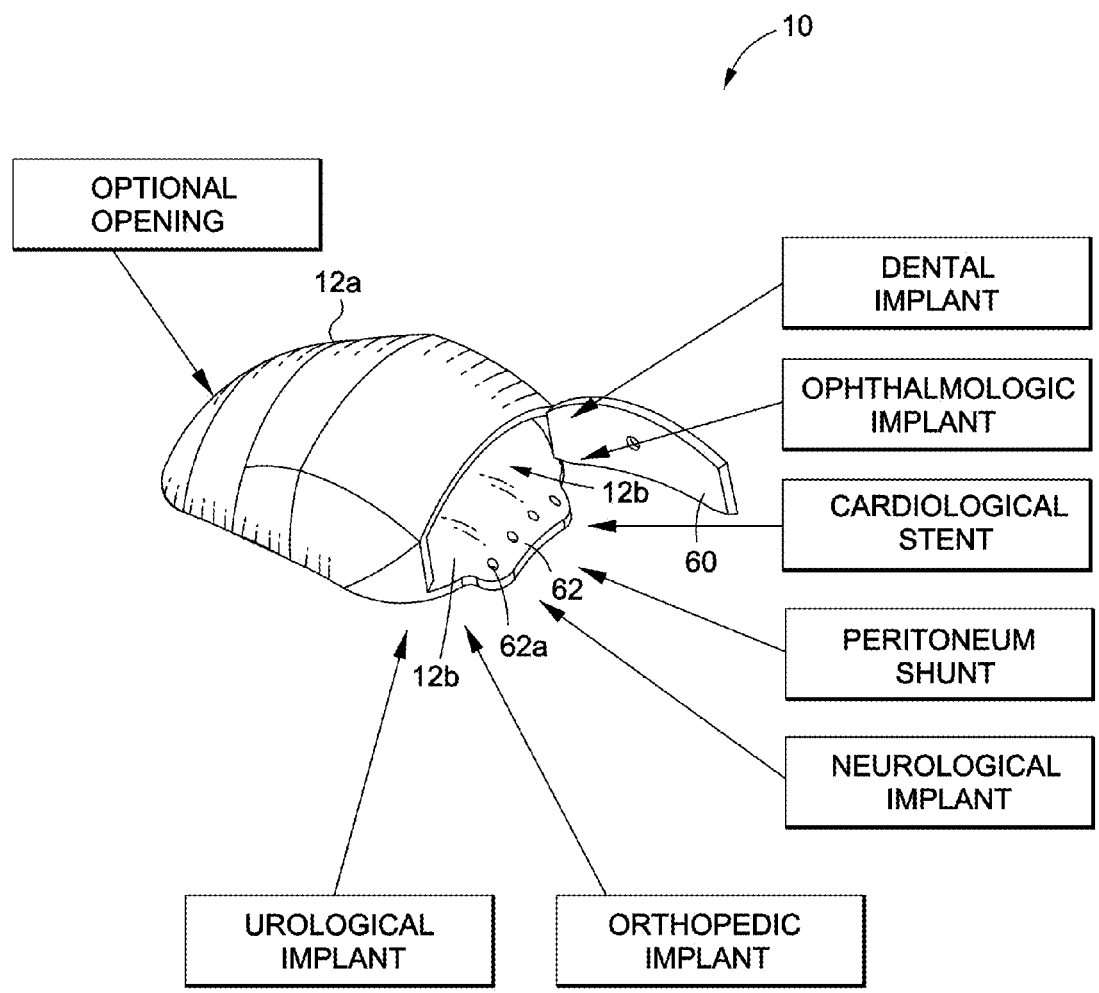
FIG. 1 is a schematic diagram depicting my implantable medical assembly.

As illustrated in FIG. 1, one embodiment of my implantable medical assembly designated by the numeral 10 includes a cover and a medical device enclosed within this chamber. Numerous types of medical devices may be used. For example, the medical device may be a cardiology device, a peritoneum shunt device, an orthopedic implant, a dental implant, a urological implant, a neurological implant, or the ophthalmological implant as illustrated herein. These various applications are not equivalent and the cover will require modification to suit each application.

FIGS. 1A through 1F depict one embodiment of a cover designated by the numeral 12a, and FIGS. 4 through 8 depict another embodiment of a cover designated by the numeral 50. Each cover 12a and 50 have an internal chamber 14, FIGS. 1F and 5, respectively. The chamber 14 includes a device retention section 18a that is upstream of a fluid retention section 18b. The fluid retention section 18b is made at least in part from a porous material that allows aqueous body fluid in the chamber 14 to flow through the pores of the material into body tissue in which the assembly 10 is implanted. The porous material promotes vascularization and inhibits or limits fibrotic encapsulation upon implantation.

Figure 4:
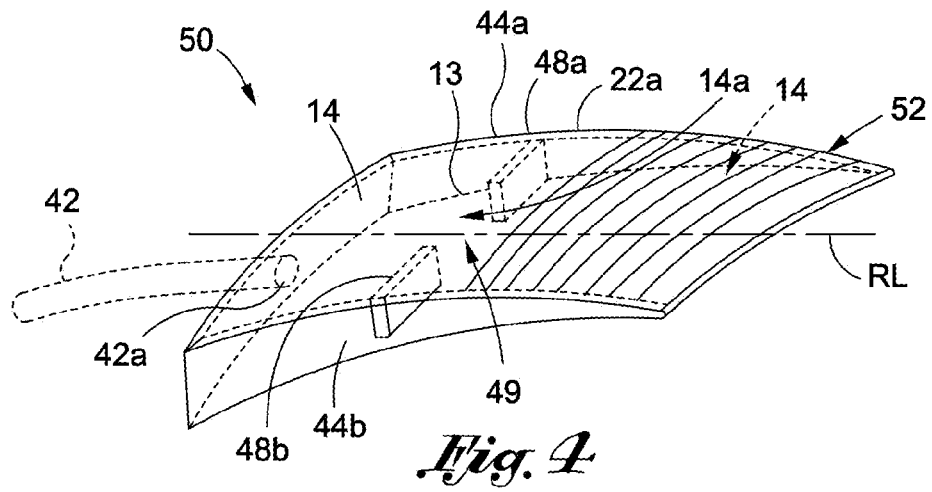
FIG. 4 is a perspective view of a cover for another embodiment of my implantable medical assembly.
Figure 5:
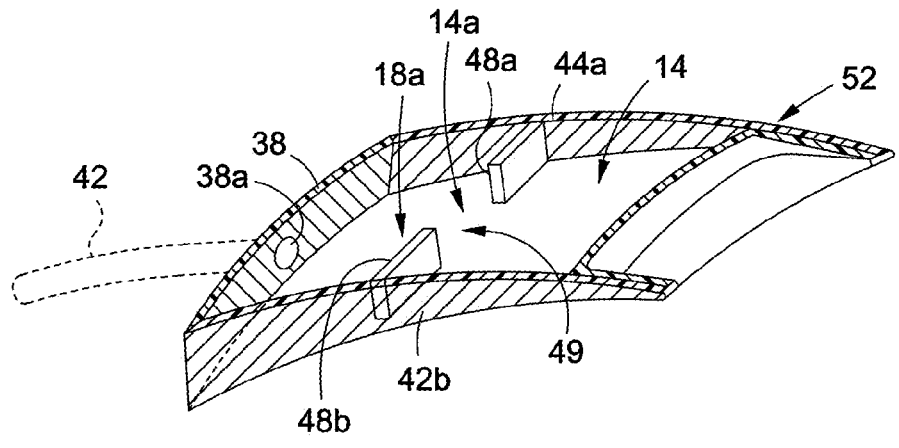
FIG. 5 is a perspective view of a frame used in the embodiment shown in FIG. 4.
Figure 6:
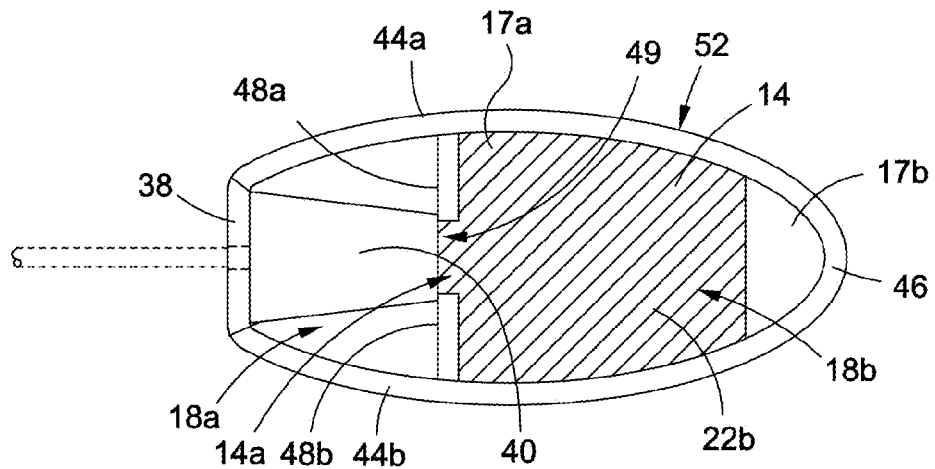
FIG. 6 is a top view of a cover for another embodiment similar to that shown in FIG. 4 with the top wall of the cover removed to show the interior of a chamber with the cover.

The cover 12 may be formed by various means such as using sheets of porous membranes as depicted in FIGS. 4 through 6 or from fused polymeric beads as illustrated by the cover 12a (FIGS. 1A through 1F). The distribution of pore size along the length of the sheet may vary. Alternately, a variable pore size distribution may be created by fusing together different diameter plastic beads 21 as depicted in FIG. 13 to mold the cover 12a from such beads. The plastic beads and membrane sheets may be selected from any biocompatible polymers. Such polymers include polyethylene, polypropylene, polyamide, polyurethane, silicone, PMMA, and pHEMA. HDPPE (high density porous polyethylene) is one material of choice to form the plastic beads and membrane sheets. The way pore size is distributed along the length of the chamber 14 is discussed subsequently in greater detail.

Figure 1C:
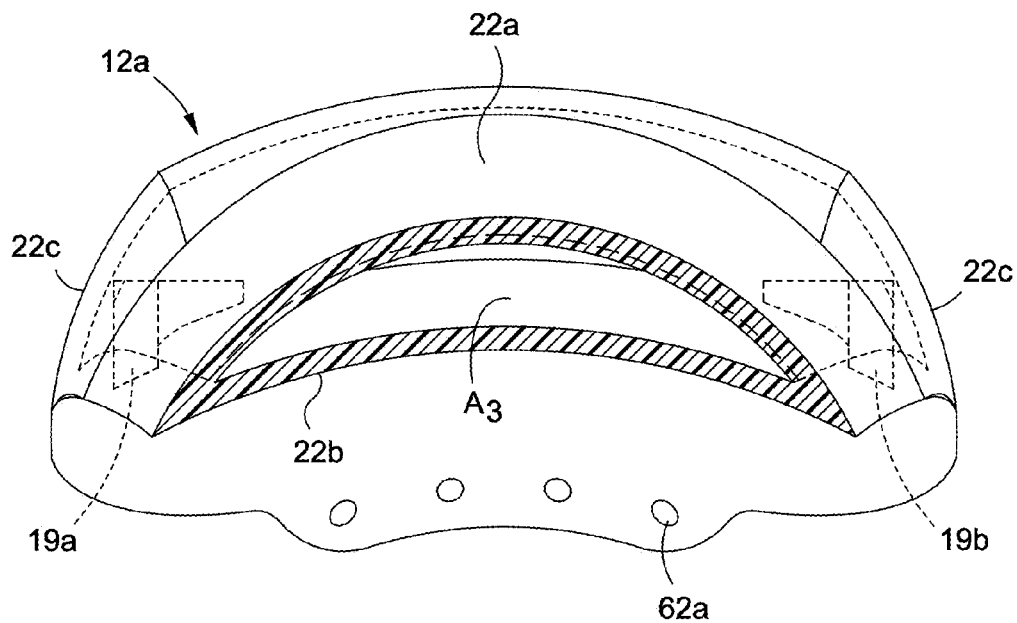
FIG. 1C is a cross-sectional view taken along line 1C-1C of in FIG. 1B.
Figure 1D:
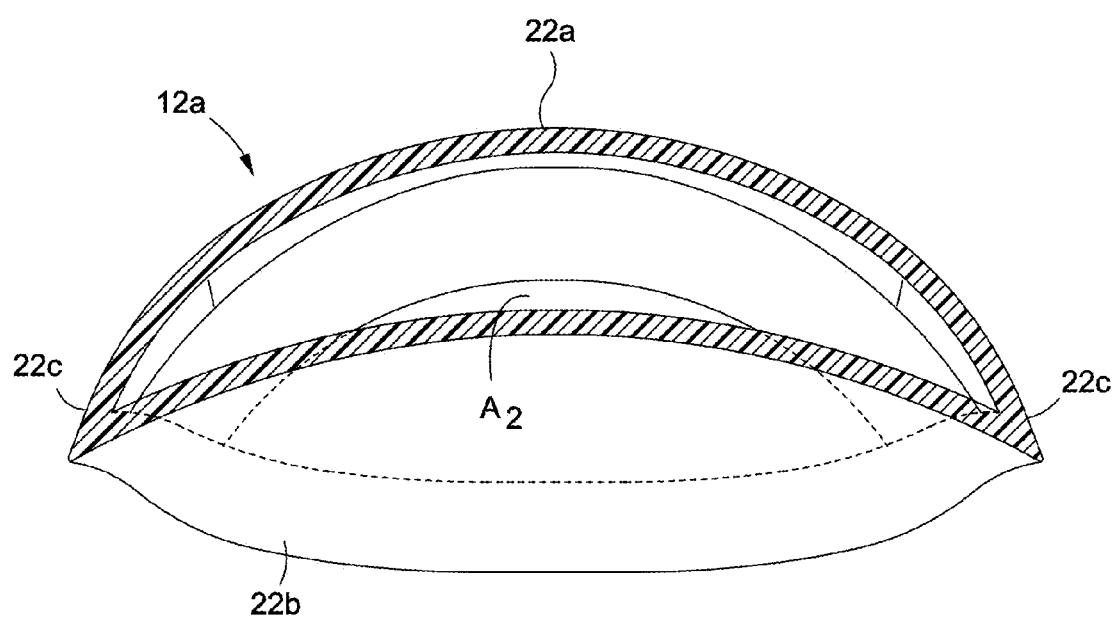
FIG. 1D is a cross-sectional view taken along line 1D-1D of in FIG. 1B.
Figure 1E:
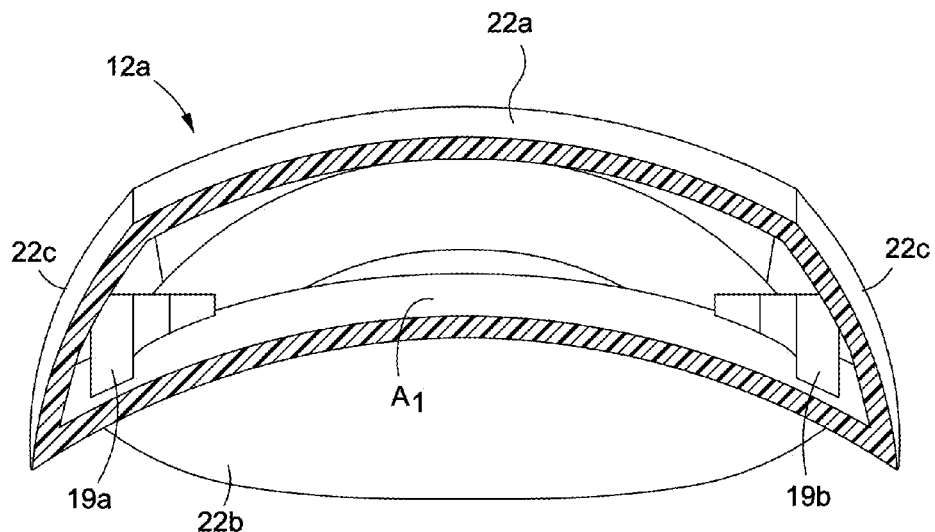
FIG. 1E is a cross-sectional view taken along line 1E-1E of in FIG. 1B.
Figure 1F:
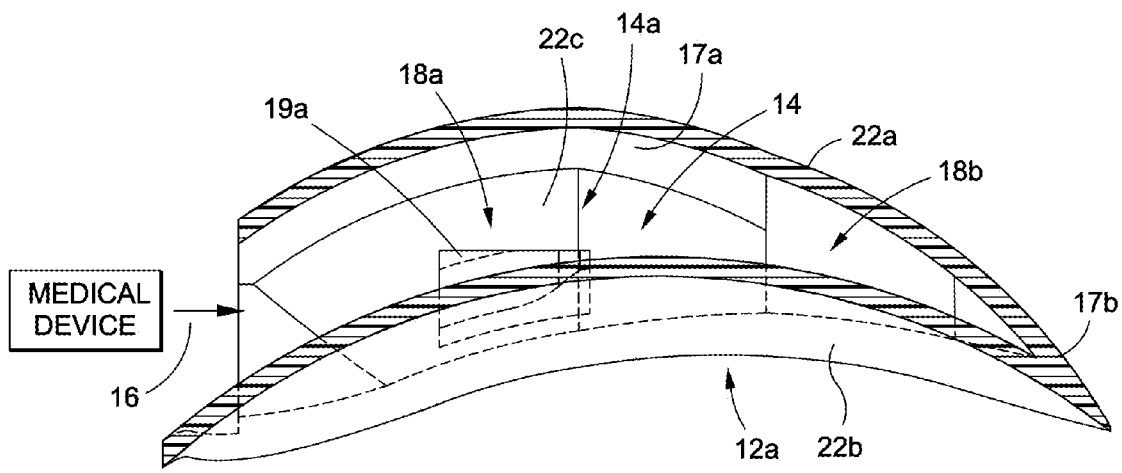
FIG. 1F is a cross-sectional view taken along line 1F-1F of in FIG. 1B.
Figure 2:
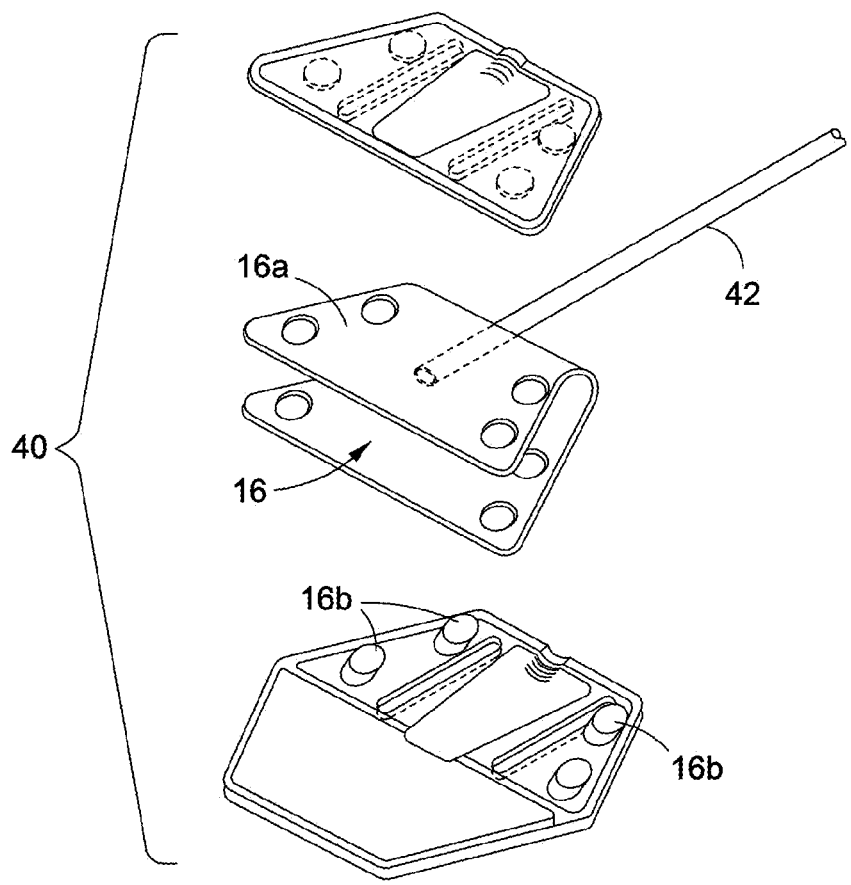
FIG. 2 is an exploded perspective view perspective of a glaucoma valve used in the embodiment of my implantable medical assembly shown in FIG. 1A.
Figure 3:
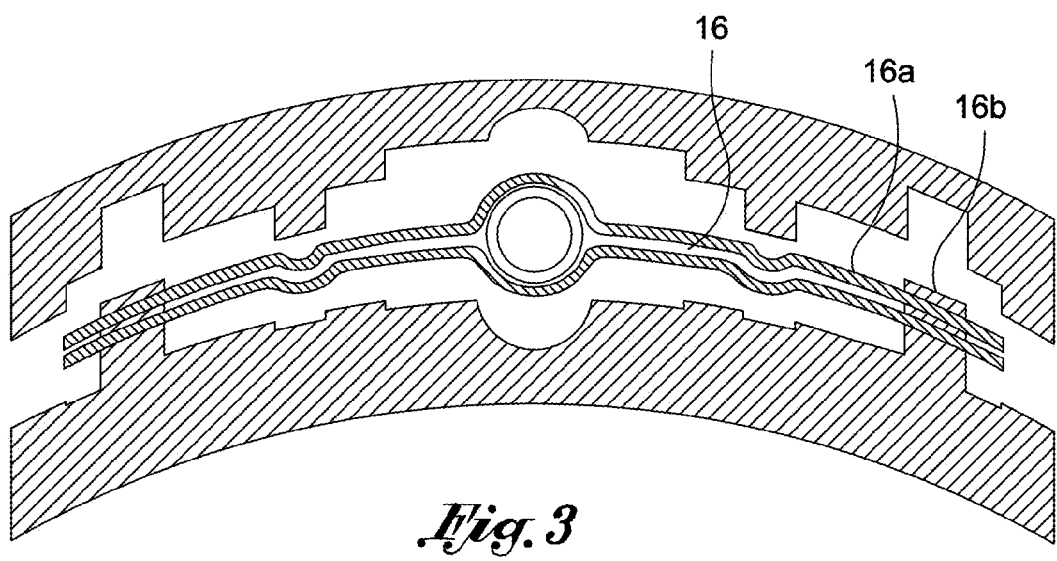
FIG. 3 is a cross-sectional view of the glaucoma valve shown in FIG. 2.

An example of a medical device advantageously used in my medical assembly 10 is an ophthalmological implant such as the Ahmed glaucoma valve 40 disclosed in U.S. Pat. No. 5,071,408 and depicted in FIGS. 2 and 3. In the Ahmed glaucoma valve 40 a folded elastic membrane 16a is sandwiched between a pair of plates with interlocking posts 16b holding the folded membrane in tension to provide a normally closed outlet 16. Aqueous body fluid flows from the outlet 16 of the medical device into the chamber 14 as depicted in FIG. 1F. The length of the cover 12 is substantially from 11 mm to 24 mm and its width is substantially from 8 mm to 16 mm.

The importance of a self-regulating valve such as the Ahmed glaucoma 40 is because the variable resistance helps to immediately bring down the IOP without delay. This helps prevent further deterioration of a patient's vision. In non-valved devices, there is no resistance provided against which those devices work. In actual practice, these non-valved devices face serious problems. One of them is the loss of the entire pressure in the eye, because there is no resistance against which the eye has to work. Loss of all pressure results in hypotony, which leads to other very serious and complicated problems. A venturi flow system was typically created in the Ahmed valve system to act like a suction pump, pulling fluid out of the eye. Hence the eye does not have to exert any extra pressure to overcome the resistance within the valve body. In actual practice the Ahmed variable resistance valve with a venturi created therein helps drain aqueous out of the eye and yet provides the necessary resistance to overcome hypotony.

FIGS. 1A through 1F

As illustrated in FIGS. 1A through 1F, one embodiment of my medical assembly uses sintered plastic beads to form a cover 12a having at least in part a porous wall. In one embodiment, the material comprises spheres made of inert biomaterials such as polyethylene, polypropylene, polyamide, polyurethane, silicone, PMMA, pHEMA, ePTFE, etc. A high melt-flow rate polymer that can be used in my medical assembly is described in U.S. Pat. No. 7,795,346B2. The cover 12a includes three sections, an upstream section I with spheres having diameters of 100 microns, an intermediate section II with spheres having diameters of 75 microns, and a downstream section III with spheres having diameters of 50 microns.

The spheres in these sections are joined together by the process described in U.S. Pat. No. 7,795,346B2. After placing the beads in a mold, the beads are heat-fused together. The cover 12a has an open mouth 12b (FIG. 1) into which a suitable medical device is inserted. The chamber 14 formed within this cover 12a has opposed sides that are fluid impermeable so the fluid exiting the outlet 16 of an inserted medical device all flows through only one porous side or only through opposed top and bottom porous sides. The sintering of the beads within the mold achieves formation of the chamber 14 having porous top wall 22a and bottom wall 22b and opposed rigid side walls 22c supporting the top and bottom walls. The radii of curvatures of the top wall 22a and bottom wall 22b are substantially from 21 mm to 38 mm. As depicted in FIGS. 1C through 1E, the area of the cross-sections $A_3$, $A_2$, and $A_1$ gradually increase from a minimal cross-section area $A_3$ near the distal end 17b of the chamber 14, to a maximal cross-section area $A_1$ near the proximal end 17a of the chamber, and an intermediate cross-section area $A_2$ between the proximal end 17a and the distal end 17b. As shown in FIG. 1E, the chamber 14 has a substantially cross-sectional trapezoidal configuration taken along a longitudinal reference line. The walls 22a and 22b are joined together to reinforce each other to resist buckling of the walls when subjected to pressure of the fluid flowing through the walls.

As depicted in FIGS. 1F, 15A and 15B, the Ahmed glaucoma valve 40 is lodged within the device retention section 18a of the chamber 14. Fluid exiting the valve 40 flows into the fluid retention section 18b of the chamber 14 and eventually through the porous walls into blood vessels 20 (FIG. 8) growing from the porous walls. A pair of opposed corner stops 19a and 19b limit the inward movement of the valve 40 so that essentially the entire valve is seated snugly within the device retention section 18a. As depicted in FIGS. 1C through 1F, the chamber 14 tapers inward from an upstream end 17a of the fluid retention section 18b to a remote, terminal downstream end 17b of the chamber. Except for any ancillary components, the entire medical device is essentially within the cover upon insertion into the device retention section 18a, in this case the Ahmed glaucoma valve 40, with only its tubular member 42 extending from the cover 12a. As shown in FIGS. 15A and 15B, a back door 60 is connected by a living hinge 60a at the open mouth 12b of the cover 12a that is integral with the chamber 14. The door 60 is closed after the medical device, for example, the valve 40, is inserted into the cover. The cover 12a may also have a suturing tab 62 with holes 62a to allow 6.0, 7.0, 8.0, 9.0 or 10.0 nylon, vicryl or any other suitable sutures to be used in anchoring my assembly to the eye.

FIGS. 4 through 8

Figure 7:
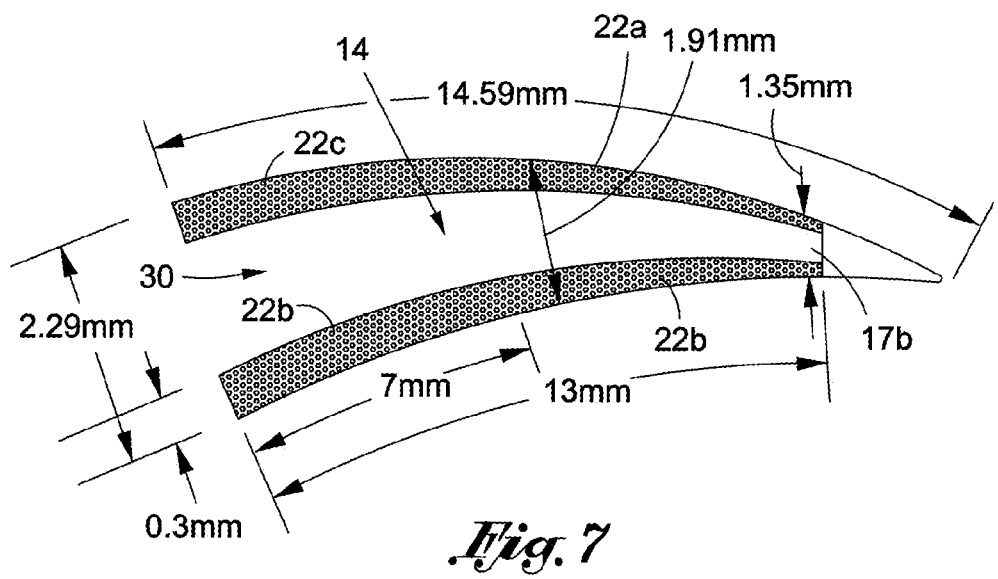
FIG. 7 is a cross-sectional view of the pair of overlying walls forming a portion of a chamber within the cover shown in FIG. 4.
Figure 8:
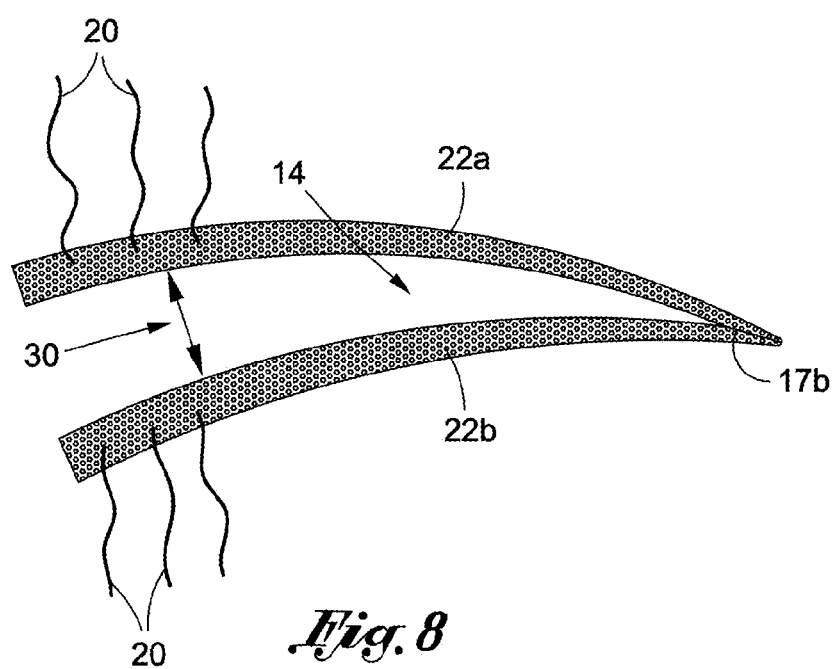
FIG. 8 is a cross-sectional view similar to that of FIG. 7 with blood vessels growing from the walls forming a portion of a chamber within the cover shown in FIG. 4.
Figure 9:
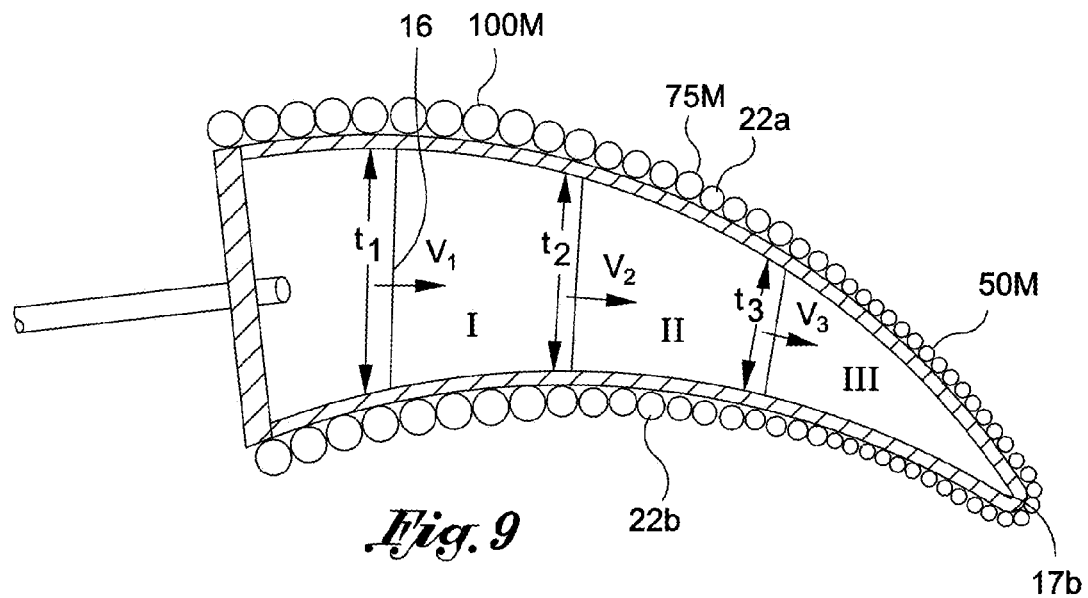
FIGS. 9 through 11 are schematic diagrams depicting the flow of fluid through the fluid retention section of the cover.
Figure 10:
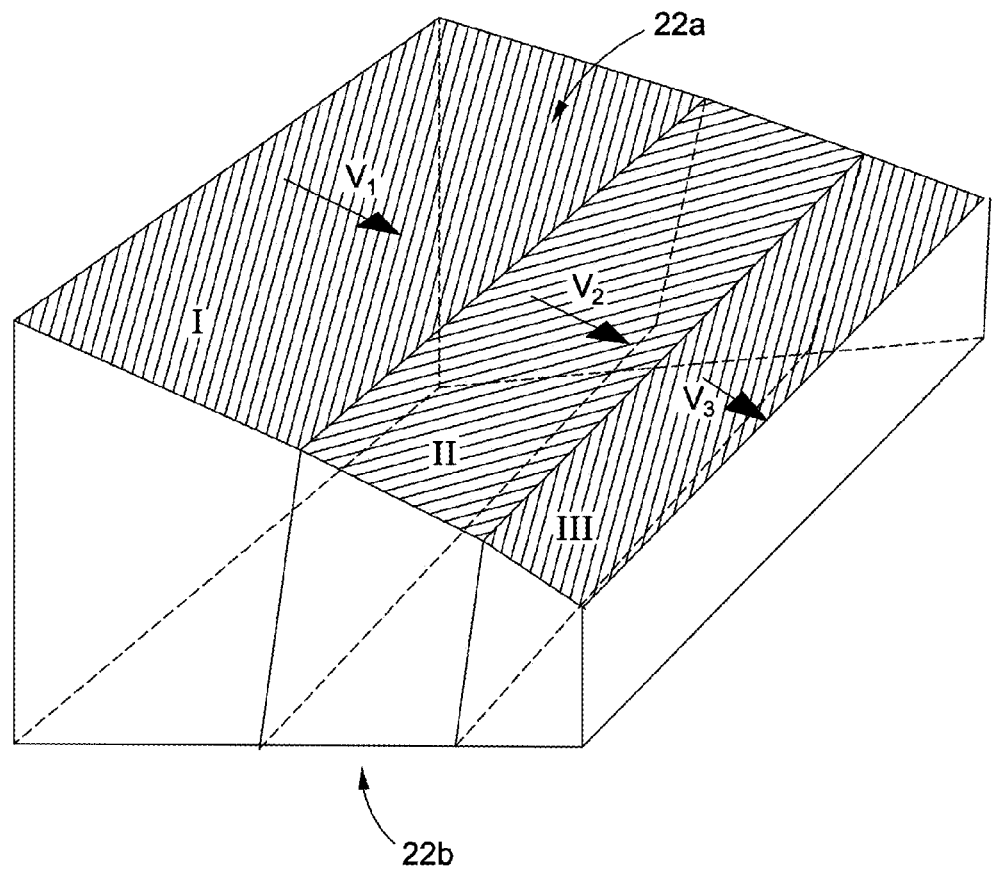
Figure 11:
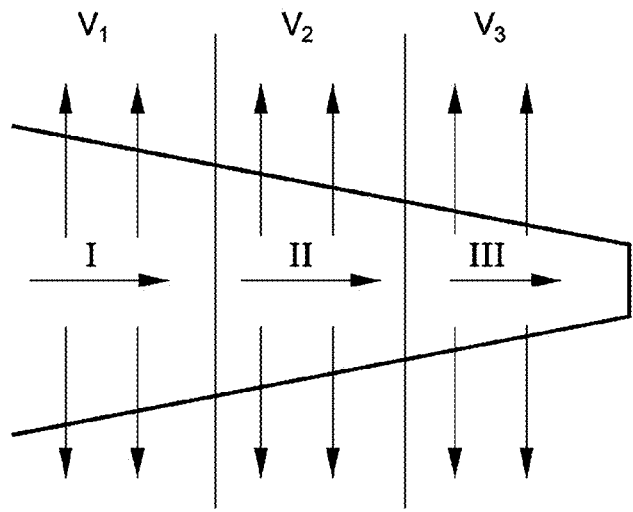
Figure 12A:
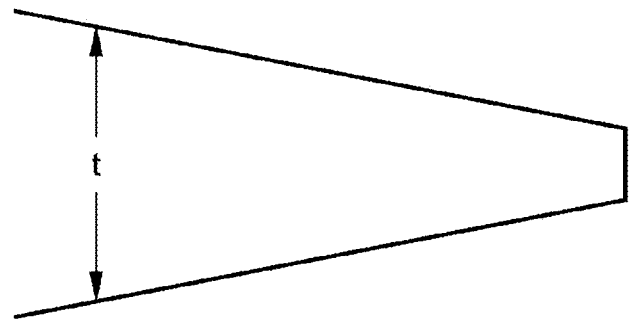
FIGS. 12A through 12B are schematic diagrams illustrating characteristics of the pores in the wall forming the chamber.
Figure 12B:
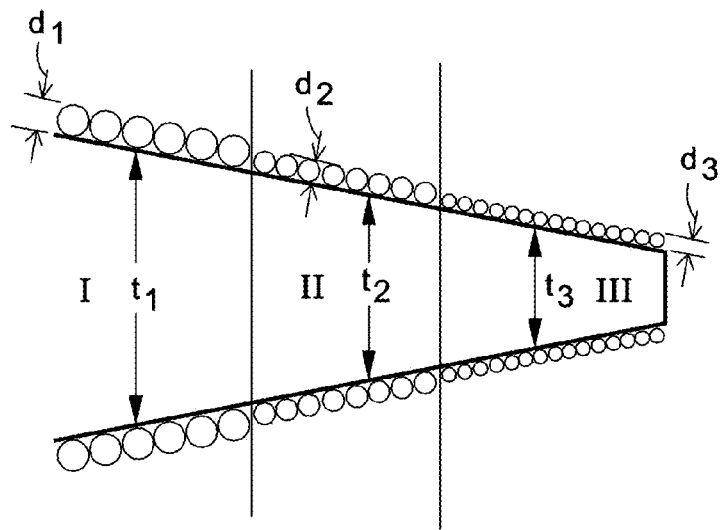

As illustrated in FIGS. 4 and 8, the cover 12 uses sheets of porous membranes to form the chamber 14. This cover 12 has opposed, top and bottom porous walls 22a and 22b curved to substantially conform to the curvature of the external surface of an eyeball. As illustrated in FIGS. 7 and 8, the walls 22a and 22b are spaced apart at the upstream end of the chamber 14 and converge at or near the proximal end 17b of the chamber. Thus, when a medical device is placed within the device retention section 18a, the outlet 16 of the medical device is at or near the entry end 14a (FIG. 1F) of the chamber 14. In this embodiment, the chamber 14 has a substantially trapezoidal cross-sectional configuration near the outlet 16 as shown in FIG. 1E, the function of which is discussed in detail subsequently. The pair of walls 22a and 22b taper inward towards each other and are the greatest distance apart near the outlet 16 to form a gap 30. The distance apart gradually decreases downstream of the outlet 16. The gap 30 substantially ranges from 0.01 to 5 mm. The thicknesses of the walls 22a and 22b are essentially equal, ranging substantially from 0.01 to 5 mm. The ratio of the thickness of the walls 22a and 22b to the gap 30 at the maximum distance between the walls ranges substantially from 1:30 to 2:1.

In this embodiment generally designated by the numeral 50 (FIG. 4), a molded plastic rigid frame 52 supports a pair of membrane sheets that form respectively the top wall 22a and the bottom wall 22b of the chamber 14. As shown in FIG. 4, the walls 22a and 22b are kept at a constant distance through supporting structure such a pair of spaced apart, curved, identically tapered plates 48a and 48b at both edges. This will ensure that when blood vessels and tissue grows into the pores there will be no buckling or sway of the top or bottom walls 22a and 22b. The exposed external edges of the cover 12 are heat treated to provide a clean, smooth surface that helps to implant the assembly 10 in between the sclera and tenons capsule.

The frame 52 may have a substantially oval perimeter as depicted in FIG. 6, except for a flat, rigid back plate 38. This back plate 38 has a central orifice 38a therein, for example, the tubular member 42 (shown in dotted lines) of the valve 40. The back plate 38 connects at their upstream ends opposed, spaced apart, outwardly curved, rigid side plates 44a and 44b that merge at their downstream ends at a rigid apex tip 46. Spaced apart intermediate plates 48a and 48b opposite each other extend inward and divide the chamber 14 into its device retention section 18a and the fluid retention section 18b. The intermediate plates 48a and 48b terminate at opposed ends and are spaced apart to provide an opening 49 aligned with and in communication with the outlet 16 of the valve 40. The valve 40 is positioned within the device retention section 18a so that the aqueous fluid exiting the outlet 16 flows directly into the fluid retention section 18b. All the plates 38, 44a, 44b, 48a and 48b are fluid impermeable and the edges of the membranes walls 22a and 22b are sealed to the plates 44a, 44b, 48a and 48b.

As depicted in FIG. 8, blood vessels 20 and connective tissue grow around and into the pores of the chamber 14, the aqueous body fluid being carried from the chamber 14 by the blood vessels. At least one wall of porous material forming the chamber 14 may have a variable pore size distribution that is selected to promote reduction of bleb formation through improved blood vessel growth. For example, a variable pore size distribution may comprise larger pores in an upstream portion of the fluid retention section 18b of the chamber 14 at or near the outlet 16 of the medical device that has been inserted into the device retention section 18a of the chamber. Smaller pores may be downstream of the upstream or distal end 17a of the fluid retention section 18b, with the smallest sized pores downstream at or near the downstream terminal or proximal end 17b of the chamber 14.

As illustrated in FIGS. 15A through 16, a medical device is placed within the device retention section 18a of the chamber 14 with the outlet 16 of the device at the entry end 14a of the chamber 14 so that fluid exiting the medical device flows into the fluid retention section 18b. For example, with the door 60 open, a free end the tubular member 42 of the Ahmed glaucoma valve 40 is fed through the orifice 60b in the door and the remainder of the valve is placed within the device retention section 18a of the chamber 14. The back door 60 is then closed, with the tubular member 42 extending from the assembly 10. The door 60 can now be sealed in a variety of ways, including with heat treatment, enclosing and substantially sealing essentially the entire the medical device within the cover 12.

Method of Use

My assembly 10 is now implanted under the cunjunctiva of the eye with the tube 42 inserted into the anterior chamber of the eye to enable the fluid in the anterior chamber to flow through the tubular member 42 through the medical device, in this example, the Ahmed glaucoma valve 40, and out the valve outlet 16. The valve 40 provides resistance to fluid flow that varies with the pressure differential across the valve. When the valve 40 opens, fluid flows through the outlet 16, through the entry end 42a and opening 49 into the fluid retention section 18b. Essentially all the aqueous fluid entering the fluid retention section 18b flows through the top and bottom walls 22a and 22b.

As illustrated in FIG. 16, a special forceps 70 is used to hold my assembly 12 when implanting it in the eye. This forceps 70 comprises a pair of opposed jaws 70a and 70b hinged at their rear ends 71 to pivot. At the jaws' forward ends opposite the ends 71 are grooves 72 along each inside length of the forward ends. The width of these grooves is such that the edges of the top and bottom walls 22a and 22b of the assembly 12 slide into the edges as shown in FIG. 16. A pair of opposed stoppers 74 in the jaws 70a and 70b engage to limit the inward movement of the jaws towards each other. The forceps 70, which may be molded from a plastic such as polypropylene or formed from a metal such as stainless steel, were developed for ease of implanting the assembly 12 and also to ensure that the doctor does not hold the assembly 12 in a manner that compresses the top and bottom walls 22a and 22b.

The following is a discussion of the flow characteristics and pore size distribution of the enclosure of my implantable medical assembly:

FLOW AND PORE SIZE CHARACTERISTICS

FIGS. 9 through 12B schematically depict a porous chamber for a medical device that has opposed tapered walls forming the chamber. The chamber produces end-to-end flow that causes downstream pressure to decrease and downstream fluid velocity to increase. In the tapered walled chamber illustrated, the distance between the walls 22a and 22b may decrease substantially linearly from near the outlet 16 of the medical device to the terminal end 17b of the chamber.

The intraocular pressure (IOP) in the eye is normally approximately between 15 to 20 mm Hg, an ideal target IOP for the device. When the IOP exceeds this approximately 8-10 mm of Hg level, the valve 40 opens. When the IOP is below this level, the valve 40 closes. The cross-sectional configuration section of the "valve system" helps to evacuate the volume of fluid coming into the valve 40. In the tapered walled chamber, velocity from end to end increases. In a parallel walled chamber, velocity decreases.

Moreover, pore size distribution along the length of the chamber wall from near the outlet 16 to the terminal end 17b may be controlled with smaller diameter pores downstream. Specifically in one embodiment, the porosity of the chamber wall is substantially from 50-100 microns. This porosity may decrease substantially linearly from near the outlet 16 to end 17b of the cover 12. The pore sizes are designed so that the volume of fluid coming into Section 1 (FIG. 9) has larger diameter blood vessels at the wall adjacent Section I, helping this largest volume to be evacuated in the same time frame as the lesser amount of fluid in downstream Section II and III. There are smaller diameter pores along the wall adjacent Section II than in upstream wall Section I, thus aiding in the growth of smaller diameter blood vessels as compared to the blood vessels growing from the wall Section I. The velocity of fluid through Section III is the greatest, but the volume of fluid is the least because the diameter of the blood vessels growing from Section III is the smallest. For example, the pores in the walls of Section I may be about 100 microns, the pores in the walls of Section II may be about 75 microns, and the pores in the walls of Section III may be about 50 microns.

The unique tapered wall of the chamber 14 creates a Bernoulli effect to keep the fluid discharging out of my assembly 10. In a steady continuous flow of a substantially frictionless incompressible fluid, the sum of the potential head, the pressure head and the kinetic head is the same as all points. Therefore, the sum of the potential pressure and kinetic heads are the same in all three Sections I, II, and III. Consequently, for a very small pressure difference there is a very large velocity difference that helps to evacuate the aqueous fluid out of my assembly 10. Moreover, there is a very definite improvement upon lowering of the IOP in the assembly 10 compared to one provided by prior art devices where higher pressures have to be exerted by the eye to evacuate fluid out of a parallel walled chamber.

Pore size along the tapered wall of the chamber 14 is illustrated in FIGS. 12A through 12C, FIG. 13, and FIGS. 14A through 14C. The relationship between the structural characteristics of the supporting structure for the porous material, the pore size, and the inter connections and the number of the blood vessels formed within the porous microassemblies of the supporting structure are closely co-related. For example, a web or open mesh may be used to support a sheet of porous material. The size of the blood vessels that grow into the porous material increases with the increase of the size of the interconnection. At the same time when the pore diameter size becomes larger than 400 microns, it does not affect the size of the bloods vessels.

Rate of growth of blood vessels may also be important. The rate of growth of blood vessels is faster within an initial 2 weeks after surgery, and then stabilizes as time goes by. Hence proper size and selection of the porous media may affect formation and transport of the required quantity of aqueous fluid in Sections I, II and III. For example, Section I may have a pore size of approximately 100 microns to evacuate properly the volume of aqueous fluid coming into this Section I; Section II may have a pore size of approximately 75 microns to evacuate properly the volume of aqueous fluid coming into this Section II; and Section III may have a pore size of approximately 50 microns to evacuate properly the volume of aqueous fluid coming into this Section III.

The size of the blood vessels is correlated to the volume of aqueous coming into and exiting each of these incremental volumetric sections. Pores size along the length of the implant is varied so that blood vessel growth is controlled to drain the different regions of the chamber uniformly. In my assembly employing the Ahmed glaucoma valve 40 within the porous enclosure, fluid from the eye has to be transferred into the systemic circulatory system through blood vessel growth. The blood vessels usually were growing into a bleb formed over the valve and through experimentation the following facts were established:

1. The size of the blood vessels found depends on the size of the pores comprising the enclosure.
2. Sections I, II, and III of the enclosure are designed as to create a forward velocity which helps to evacuate the trapezoidal sections I, II, and III. This type of typical trapezoidal section helps to avoid fluid resistance.

Pore sizes and the relationship between variable pore size, and blood vessel growth were determined through animal trials. Pore size ranging between 20 microns to 100 microns were tested to see which is optimum size of pores for which only blood vessels will grow, with the penetration of any other tissue. The best-suited pore sizes in this rabbit study were found to be between 50 microns to 100 microns.

If the total volume of fluid coming into the valve is approximately 0.2 cubic centimeters (cc), approximately 0.12 cc will be in Section I, approximately 0.06 cc in section II, and approximately 0.02 cc in Section III. Based on the volume of fluid entering in these sections, the pore sizes of the spheres were calculated. In Section I, which is closest to the valve, the size of the spheres created pores of approximately 100 microns. In Section II, the spheres created a pore size of approximately 75 microns, and in Section III the spheres created a pore size of approximately 50 microns.

The volume of fluid flowing through Sections I, II, and III are always constant per unit of time. Hence the equation of continuity:

$$A_1 V_1 = A_2 V_2 = A_3 V_3 = \text{CONSTANT where } A_1 > A_2 > A_3 \text{ and } V_3 > V_2 > V_1$$

Hence, as the cross sectional area of the Sections I, II, and III decreases, the velocity of the fluid increases, hence the volume of fluid exiting the sections remains constant per unit time.

ANIMAL EXPERIMENTS

My medical assembly of a valved drainage valve enclosed in a porous cover was tested in pigs and rabbits. The roof and floor of the cover were porous while the sides were smooth and non-porous. This configuration ensures that the implant was easy to insert and that fluid outflow from my medical assembly occurs only through the porous regions of the cover. Upon histological examination of the tissue growth around the implanted assembly in pigs and rabbits, it was found that the type of tissue growth around the porous roof of the cover helped facilitate fluid outflow. Around the roof of the implanted assembly there was little sign of typical fibrous tissue growth. Rather the tissue response can be described as a low level chronic inflammatory response in which there are few collagen fibers present. Around the nonporous regions of the implant, thick collagen fibers were present. These findings are summarized in the photographic images shown in FIGS. 17-19.

Figure 17:
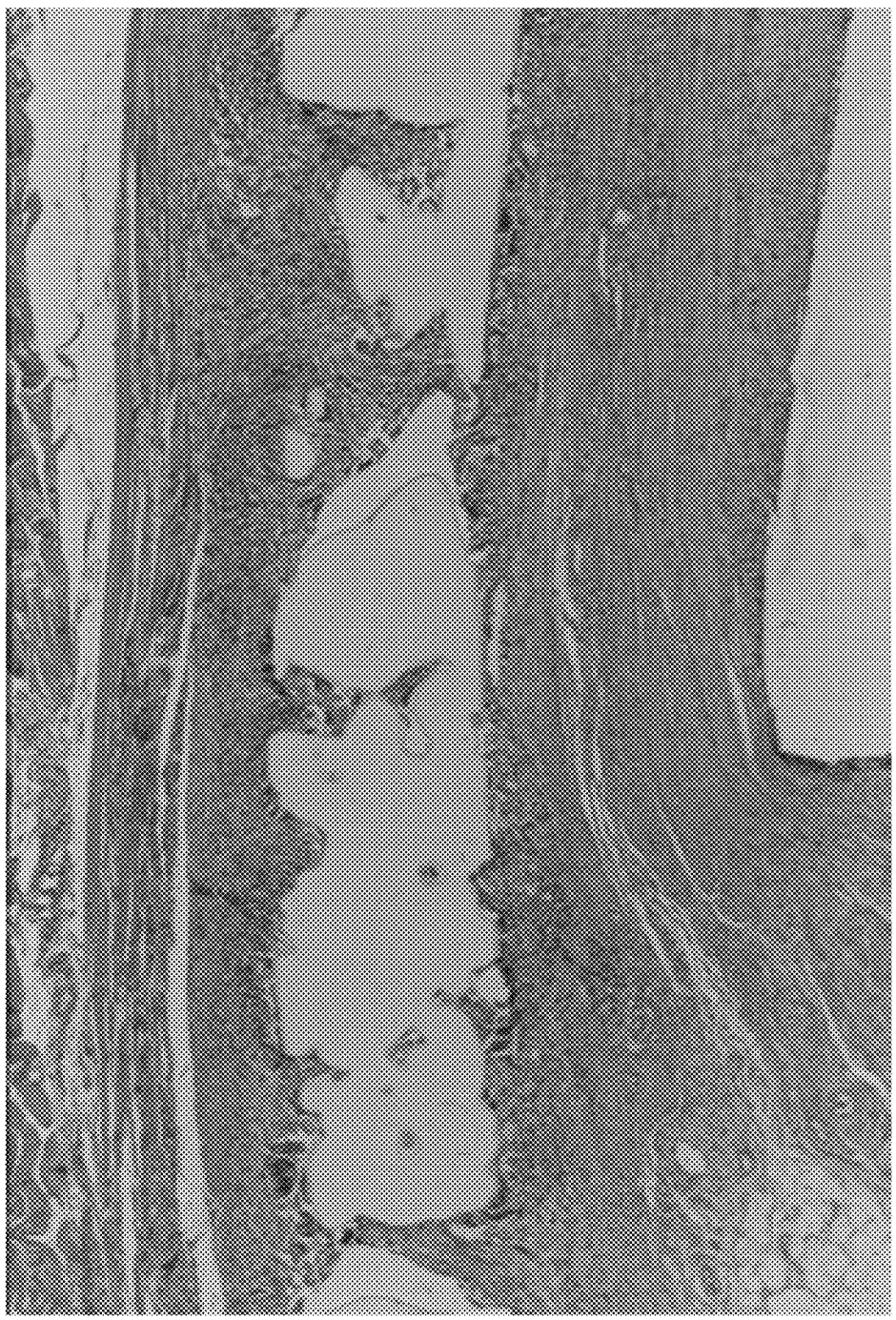
FIG. 17 is a section photograph showing the histology of a pig's eye implanted with my medical assembly for a period of six months.

FIG. 17 shows the histology from the eye of a pig implanted with my medical assembly for a period of 6 months. This photographic section shows spaces occupied by porous polymer surrounded by inflammatory granulomatous tissue growth that is permeable to fluid flow. Note the lack of thick, fluid impermeable, compact collagen fibers.

Figure 18:
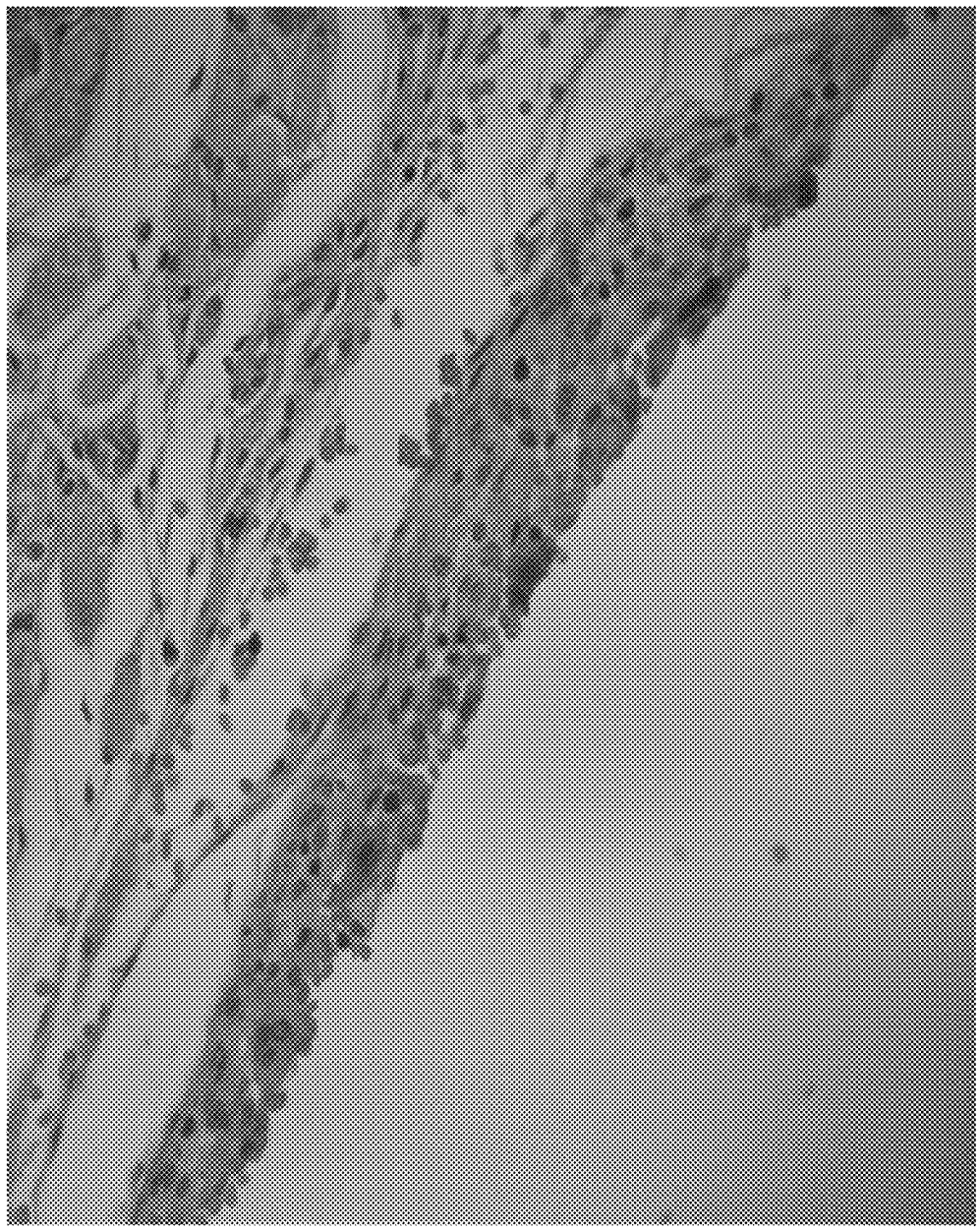
FIG. 18 is a section photograph showing tissue surrounding the porous top of the chamber of a rabbit's eye implanted with my medical assembly for a period of two months.

FIG. 18 shows a section of eye tissue from a rabbit implanted with my medical assembly for 2 months. The tissue shown surrounds the porous roof of the device cover. A chronic inflammatory response is shown with the presence of red blood cells from newly formed blood vessels. Note the lack of collagen fibers.

Figure 19:
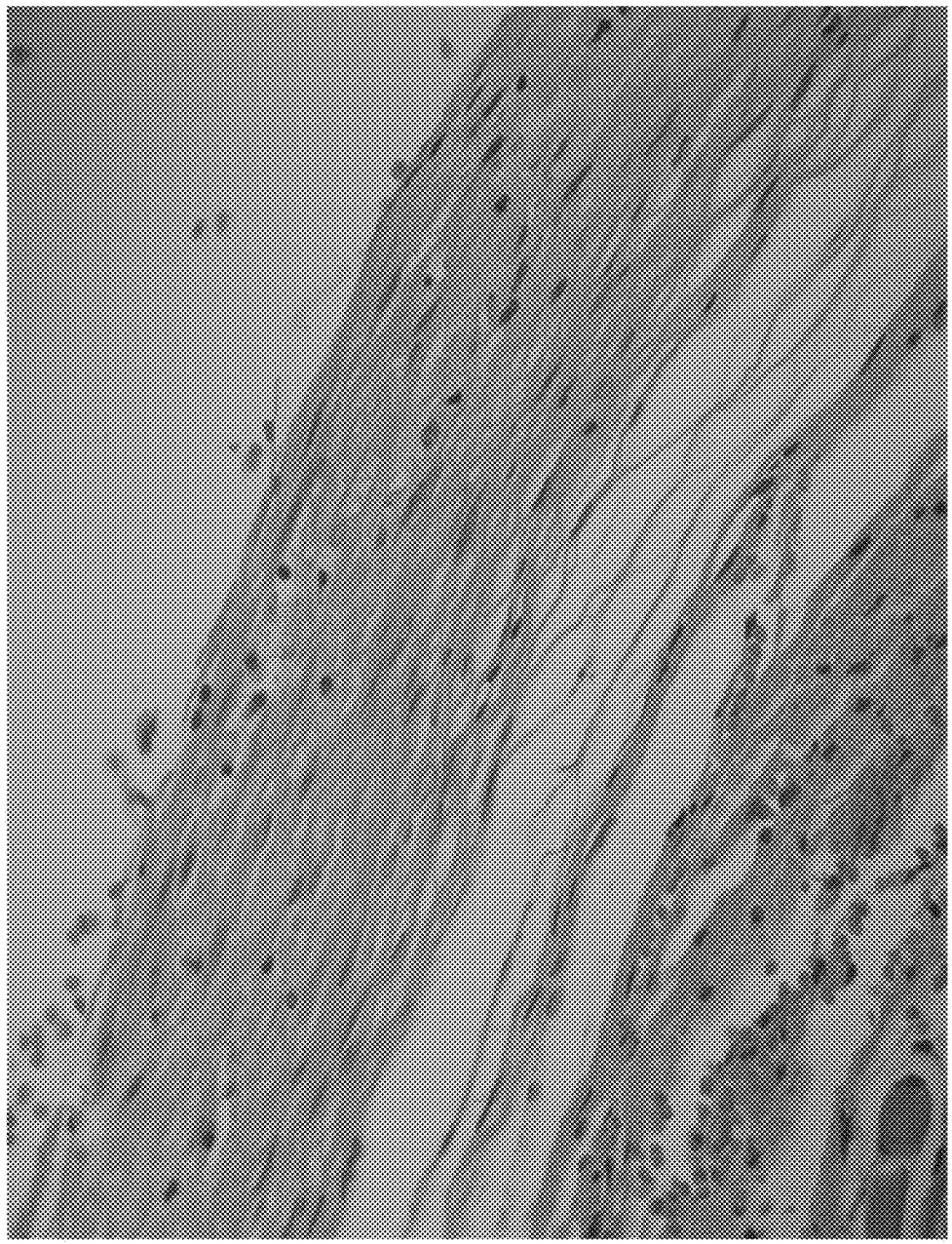
FIG. 19 is a section photograph showing tissue surrounding the porous bottom of the chamber of a rabbit's eye implanted with my medical assembly for a period of two months.

FIG. 19 shows a section of eye tissue from a rabbit implanted with the medical assembly for 2 months. The tissue shows a non porous region of the device cover. A thick growth of fluid impermeable connective collagen tissue is shown. This is a result of the smooth non-porous surface found on the side of the implant.

The growth of tissue that is loose and vascularized and the inhibition of thick collagen formation are important to optimal functioning of my assembly. However, excessive tissue growth through the porous walls and into the fluid filled cavity of the chamber could prevent the medical device from draining fluid sufficiently to lower IOP. Studies with high density porous polyethylene similar to the type used in my assembly have shown that complete tissue growth through a 3 mm sheet of the porous material occurs over a 5 to 12 week period (Sauer, 1978). In a study in human patients, fibrovascular growth through 6 mm of an HDPE ophthalmic socket implant occurred in 4 months (Karesh, 1993). To prevent tissue from filling the cavity of the chamber in my assembly, a minimum distance between the top and bottom walls of the porous chamber must be maintained. Furthermore, the distance needed to prevent tissue growth into the fluid cavity is related to the velocity of flow and therefore the pore size. If the chamber can be divided into three sections of equal length, the average pore size needed to maintain a minimum velocity is related to the distance between the top and bottom walls by a constant k. This relationship can be described by the following equation $$\frac{d_1}{t_1} = \frac{d_2}{t_2} = \frac{d_3}{t_3} = k$$

This is a very important finding. Based on this the size of the average pore size was calculated to encourage the growth of specific size of blood vessels that will be able to take the volume of aqueous out of sections I, II, and III. The proper ratio of the diameter of the pores to the distance t is required so that the tissue growth does not cross from one side to the other of the cover.

Based on the volume of incoming aqueous, different pore sizes along the lengths of the device were considered. Further rabbit experiments using 20 microns to 100 microns pore sizes helped to establish the right size of spheres to be used. The 100 micron pore size was found to be suitable for Section I where larger blood vessels grew and carried a larger quantity of aqueous fluid out of this section I. In Sections II and III there was slightly lesser volume of incoming aqueous so smaller size pores were needed. Section II pore size is 75 microns, and Section III pore size is 50 microns. Research has shown that pore size is a critical determinant of tissue growth in porous material. A minimum pore size of around 40 micrometers is needed for some vessel and tissue in growth (Shanbhag, 1990). Larger pore sizes up to 400 micrometers ensure more consistent tissue growth (Klawitter, 1976) (Feng, 2011). Ten rabbits were implanted with modified Ahmed Glaucoma valves enclosed in a porous material that had variable pore sizes between 50-150 um. The IOP after 6 weeks was found to be 9.1+1.8 mm of Hg. Histology showed where there were bigger pores, larger blood vessels grew.

Another important in vivo finding was investigated. Rabbits were injected through the valve with a fluorescent dye. The dye was immediately detected in the rabbit's urine showing that the dye had entered the blood stream through blood vessels.

HUMAN IMPLANTS

Upon receiving regulatory approval of the assembly device consisting of the Ahmed Glaucoma Valve enclosed in a porous cover, human studies were initiated. So far, results of 50 patients over 6 months have been very promising. Usually the blebs in glaucoma drainage device patients are fairly large and in some patients bulge out and can be easily discerned visually. In these patients there were no signs of bleb formation. Also, it was found the pressures remained well within the desired range of 10 to 15 mm of Hg over a substantial period for many patients. This clearly demonstrates that my assembly and method help to lower the IOP in glaucoma patients.

CONCLUSION

Using my medical device to treat glaucoma according to my method comprises enclosing a glaucoma drainage device, for example, a valve, within a porous chamber. This avoids hypotony yet removes fluid in a controlled manner by means of the encased non-obstructive, self-regulating valve, with minimal resistance to flow. A very low resistance outside of the valve due to the porous chamber produces lower pressure within the anterior of the eye. The longitudinal velocity through my assembly 10 becomes the governing factor in evacuating fluid from the porous chamber. Furthermore, the blood carrying capacities of different blood vessels along the length of the tapered chamber wall help carry different volumes through my assembly 10. My assembly 10 systematically dispenses incoming and outgoing aqueous fluid through larger blood vessels at sections required to disperse larger volumes of aqueous fluid. Larger diameter blood vessels grow adjacent larger volumetric sections. Consequently, a post-operative hypertensive phase, in which IOP rises during a phase in wound healing is avoided or minimized. In my assembly and method a very low outside resistance helps to create a dynamic flow and to maintain low IOP by a controlled velocity gradient and blood absorption system, such that when more fluid comes into a downstream section the section has the capacity to disperse it.

My assembly 10 may be viewed as a low resistance pump that pulls aqueous fluid from of the eye. Fluid velocity through the assembly 10 becomes a controlling factor to maintain proper pressure control. If the quantity of incoming fluid is large, a larger outgoing velocity is provided within the tapered chamber to evacuate the flow. The tapered walls of the chamber 14 that form a trapezoidal cross-section maintain the desired velocity gradient of fluid flow from end to end of the chamber. Depending on the quantity of aqueous fluid coming into the upstream end of the chamber, different diameters of the blood vessels are formed due to the variable pore diameter sizes along the length of the chamber 14. The pressures P along the length of the chamber 14 decrease from $P_1 > P_2 > P_3 > P_4 > 0$.

Broadly, my method creates a system of variable pore sizes depending on the requirement of the size of the blood vessel growth for transport of body fluid. It has clinical application in stents placed in arteries and veins. It has application in brain implants used to treat conditions like hydrocephalus, meningitis, liver hepatitis, and anastromosis of blood flow in case of postal hypertension and bone implants. It is not limited to human application but can also be used as a prosthesis for animals or other biological uses.

Note, in my medical assembly, where a drainage implant is covered by a variable pore size cover:
1. The variable pore size outer casing lowered the tissue resistance to fluid outflow from the drainage valve while the drainage implant prevented over drainage.
2. A variable trapezoidal outer porous casing was created to maintain proper velocity to help push the fluid out of this trapezoidal section because of velocity difference.
3. Different sizes of blood vessel growth over the length of the porous chamber help dissipate different volumes of fluid out of the variable sections in the chamber.
4. The pore sizes that create the appropriate sized blood vessels along the length of the assembly were helpful in removing the necessary amounts of fluid from sections of the chamber.

My assembly and method provides a much improved system where the porous material has the capability to channel fluid through controlled blood vessel growth resulting in lower outflow resistance and better IOP control in glaucoma patients.

SCOPE OF THE INVENTION

The above presents a description of the best mode I contemplate of carrying out my medical method, assembly and system, and of the manner and process of making and using them in such full, clear, concise, and exact terms as to enable a person skilled in the art to make and use. My medical method, assembly and system are, however, susceptible to modifications and alternate constructions from the illustrative embodiments discussed above which are fully equivalent. Consequently, it is not the intention to limit my medical method, assembly and system to the particular embodiments disclosed. On the contrary, my intention is to cover all modifications and alternate constructions coming within the spirit and scope of my medical method, assembly and system as generally expressed by the following claims, which particularly point out and distinctly claim the subject matter of my invention:

The invention claimed is:
1. A medical assembly comprising
a medical device from which fluid flows, and
a cover for the medical device including a chamber having an upstream section and a downstream section said medical device being positioned in the u stream section so fluid escaping from the device flows first into an upstream end of the downstream section and into the downstream section, flowing towards a downstream end of the chamber,
said downstream section of the chamber having at least a partially porous portion decreasing in cross-sectional area from said upstream end to the downstream end so fluid flows at an increasing velocity as said fluid exits the device and flows downstream towards the downstream end, the porous portion of the chamber has a porosity that varies in stages, and where upstream stages of the porous portion of the chamber have a greater porosity than downstream stages of the chamber.

2. The medical assembly of claim 1 including pores in a stage nearest the upstream end ranging in pore size from 75 to 400 microns, pores in a middle stage ranging in pore size from 50 to 200 microns, and pores in a stage nearest to the downstream end ranging in pore size from 25 to 125 microns.

3. The medical assembly of claim 1 including a first stage of the porous portion of the chamber having a volume of 0.12 cubic centimeters, a second stage of the porous portion of the chamber having a volume of 0.06 cubic centimeters, and a third stage of the porous portion of the chamber having a volume of 0.02 cubic centimeters.

4. A medical assembly comprising
a medical device from which fluid flows, and
a cover for the medical device including a chamber having an upstream section and a downstream section said medical device being positioned in the upstream section so fluid escaping from the device flows first into an upstream end of the downstream section and into the downstream section, flowing towards a downstream end of the chamber,
said downstream section of the chamber having at least a partially porous portion decreasing in cross-sectional area from said upstream end to the downstream end so fluid flows at an increasing velocity as said fluid exits the device and flows downstream towards the downstream end,
the porous portion of the chamber has a porosity that varies in stages, and
where each stage includes pores having a uniform diameter with the pores in the downstream stages having diameters at least 25 percent less than a preceding stage.

5. A medical assembly comprising
a medical device from which fluid flows, and
a cover for the medical device including a chamber having an upstream section and a downstream section that is at least partially porous,
said medical device being positioned in the upstream section so fluid escaping from the device flows first into an upstream end of the downstream section and into the downstream section, flowing towards a downstream end of the chamber,
said downstream section of the chamber configured so fluid flows at an increasing velocity as said fluid exits the device and flows downstream towards the downstream end,
said porous section having a porosity that varies in stages where upstream stages of the porous portion of the chamber have a greater porosity than downstream stages of the chamber.

6. A medical assembly comprising
a medical device from which fluid flows, and
a cover for the medical device including a chamber having an upstream section and a downstream section that is at least partially porous,
said medical device being positioned in the upstream section so fluid escaping from the device flows first into an upstream end of the downstream section and into the downstream section, flowing towards a downstream end of the chamber,
said downstream section of the chamber configured so fluid flows at an increasing velocity as said fluid exits the device and flows downstream towards the downstream end,
said porous section having a porosity that varies in stages where each stage includes pores having a uniform diameter with the pores in downstream stages have diameters at least 25 percent less than a preceding stage.

* * * * *